United States Patent

Kotick et al.

[11] 4,230,712
[45] Oct. 28, 1980

[54] 7-METHYL-8β-LOWER ALKYL OR 7-METHYL-8-LOWER ALKYL B/C CIS OR TRANS MORPHINAN-6-ONE COMPOUNDS AND THERAPEUTIC METHOD OF TREATING PAIN EMPLOYING THEM

[75] Inventors: Michael P. Kotick, Elkhart, Ind.; Robert N. Schut, Edwardsburg, Mich.; Joseph O. Polazzi; David L. Leland, both of Elkhart, Ind.

[73] Assignee: Miles Laboratories, Inc., Elkhart, Ind.

[21] Appl. No.: 40,664

[22] Filed: May 21, 1979

Related U.S. Application Data

[63] Continuation-in-part of Ser. No. 876,639, Feb. 10, 1978, abandoned.

[30] Foreign Application Priority Data

| Dec. 12, 1978 | [CA] | Canada | 317750 |
| Dec. 18, 1978 | [IL] | Israel | 56245 |
| Jan. 9, 1979 | [DE] | Fed. Rep. of Germany | 2900644 |
| Jan. 9, 1979 | [MX] | Mexico | 7636 |
| Jan. 25, 1979 | [FR] | France | 79 01967 |
| Feb. 6, 1979 | [GB] | United Kingdom | 7904030 |
| Feb. 8, 1979 | [AU] | Australia | 44089/79 |
| Feb. 8, 1979 | [JP] | Japan | 54-12883 |

[51] Int. Cl.³ .................. A61K 31/485; C07D 221/28
[52] U.S. Cl. ..................................... 424/260; 546/074
[58] Field of Search ........................ 546/74; 424/260

[56] References Cited

U.S. PATENT DOCUMENTS

| 2,178,010 | 10/1939 | Small et al. | 546/45 |
| 2,766,245 | 10/1956 | Gates, Jr. | 546/74 |
| 3,211,738 | 10/1965 | Sawa et al. | 546/74 |
| 3,285,922 | 11/1966 | Gates, Jr. | 546/74 |
| 3,300,500 | 1/1967 | Sawa et al. | 546/74 |

Primary Examiner—Donald G. Daus
Assistant Examiner—D. Rivers
Attorney, Agent, or Firm—Jerome L. Jeffers

[57] ABSTRACT

Disclosed are 7-methyl, 8β-lower alkyl and 7 methyl-8-lower alkyl substituted B/C Cis or Trans morphinan-6-one compounds characterized by the structural formula:

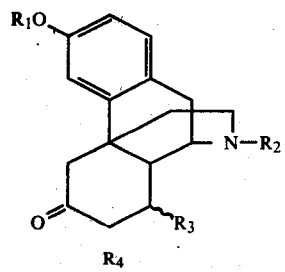

Specific compounds, included within the scope of the foregoing general formula wherein $R_1$ is H or methyl, $R_2$ is cyclopropylmethyl or cyclobutylmethyl, $R_3$ is H, methyl, ethyl or n-propyl and $R_4$ is H or methyl are useful as mixed analgesics/narcotic antagonists.

44 Claims, No Drawings

7-METHYL-8β-LOWER ALKYL OR 7-METHYL-8-LOWER ALKYL B/C CIS OR TRANS MORPHINAN-6-ONE COMPOUNDS AND THERAPEUTIC METHOD OF TREATING PAIN EMPLOYING THEM

BACKGROUND OF THE INVENTION

This application is a continuation-in-part of co-pending application Ser. No. 876,639 filed on Feb. 10, 1978 and now abandoned.

FIELD OF THE INVENTION

Morphine is a well known narcotic analgesic having the structural formula:

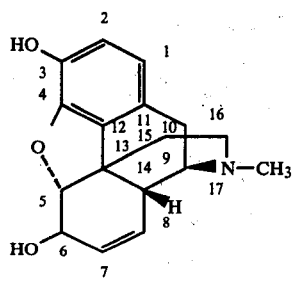

The compounds of this invention are structurally related to morphine and are named according to the morphinan system of nomenclature using the morphinan nucleus which is shown below:

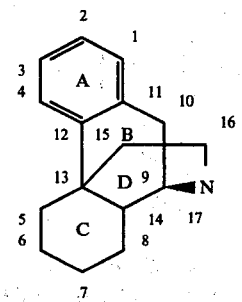

The numbering and stereochemical placement of atoms in the morphinan system is the same as that depicted for morphine. A dashed line is used to represent a covalent bond projecting below the plane of a reference atom while a wedged or heavily accented line signifies a covalent bond above such plane. The compounds of this invention have the same stereochemical placement of atoms as depicted for morphine unless otherwise indicated. In some structures, such as the general formula appearing on Page 1 hereof, a serpentine line (~) denotes orientation of a covalent bond either above or below the plane of reference.

Another feature of the stereochemistry of the morphinan nucleus is that when the hydrogen in the 14-position is in the β orientation the compounds have the same B/C ring junction as the naturally occurring morphine alkaloids and are referred to as the B/C cis isomers. Conversely, when the 14-hydrogen atom is in the α orientation the compounds are in the B/C trans configuration and are referred to as isomorphinans.

Morphine and its structurally related relatives are used primarily as analgesics. While extremely effective for the relief of moderate to severe pain these compounds are narcotic and most possess dependence-inducing ability and produce other side effects such as emesis, constipation, sweating, respiratory depression and myosis which make them less than ideal analgesics. It is impossible to predict, based on structure alone, whether a particular morphine-like compound will act as an analgesic (agonist), a narcotic antagonist or possess a combination of these properties since very minute structural modification in the molecule can significantly change the way it affects an individual to which it is administered. A compound with the appropriate profile of analgesic (agonist) and narcotic antagonist actions has potential for treatment of moderate to severe pain without the liability of drug dependence or drug abuse.

PRIOR ART

The 7,8-didehydro-3-methoxy-17-methylmorphinan-6-one used as the starting material for some of the analgesic narcotic antagonists described herein is described by Sawa and Maeda (Tetrahedron 20: 2247 [1964]), (hereinafter referred to as "SAWA").

U.S. Pat. No. 3,654,280 (Y. Sawa, et al., assigned to Shionogi & Co., Ltd., published Apr. 4, 1972; hereinafter referred to as "SHIONOGI") reports narcotic antagonist activity for certain 17-allyl, 17-dimethylallyl or 17-cyclopropylmethyl substituted 3-hydroxy-morphinan-6-one compounds related to the compound reported by SAWA.

Morphinan-6-one compounds substituted in the 8-position with an oxygen atom, as in a hydroxyl group or ether group, have been reported by Tada et al. (Tetr. Lett., 1805 [1960]). Seki (Chem. Pharm. Bull. 14: 445 [1966]) reports a deoxytetrahydrocodeine compound substituted in the 8-position with a pyrrolidinyl group.

Small et al disclose in U.S. Pat. No. 2,178,010 (issued Oct. 31, 1939) the reaction of dihydrothebaine:

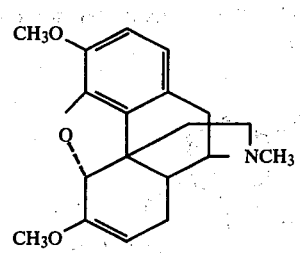

with methylmagnesium iodide in refluxing ether solution for 108 hours to give, after workup which includes acid hydrolysis, a mixture from which may be isolated in 45-58% crude yield (15-17.5% recrystallized)methyldihydrothebainone:

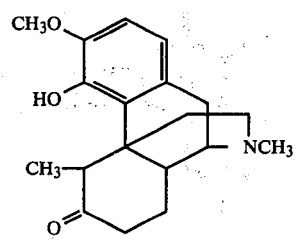

and a 9-11% yield (5-6% recrystallized) of isomethyldihydrothebainone:

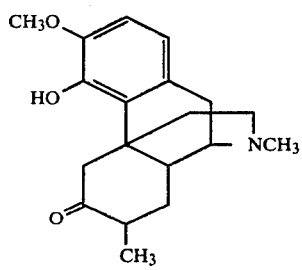

VI

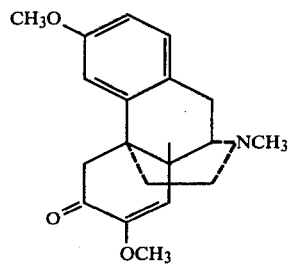

X

Small et al. also report in J. Org. Chem., 3, 204 (1938) the reaction of dihydrocodeinone enol acetate:

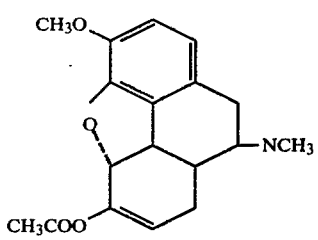

VII with methylmagnesium iodide for 24 hours in boiling ether to give a 74% yield of V and some VI with no mention of its exact percent yield. It should be noted that the 7-methyl compound VI is the minor product of these reactions and is difficult to obtain. This is in contrast to the presently reported facile introduction of a methyl group, with concurrent 4,5-epoxy bond cleavage, into the 7-position of the morphinane nucleus.

The introduction of a 7-ketone into the morphinane nucleus with concurrent cleavage of the 4,5-epoxy bond has been reported by Rearick and Gates in Tetrahedron Letters, 507 (1970). They report that treatment of 14-bromocodeinone:

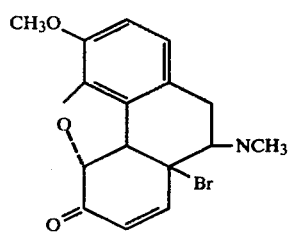

VIII with Claisens alkali gives the 7-keto morphinane IX:

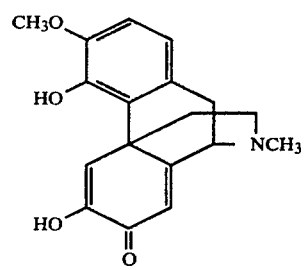

IX

Sawa et al report the preparation of desoxysinomenine characterized by the formula:

and desoxydihydrosinomenine characterized by the formula:

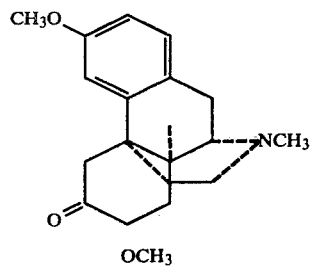

XI in Tetrahedron, 15, 144 (1961) from the naturally occuring alkaloid, sinomenine:

CH₃O

XII

HO

NCH₃

O

OCH₃

Introduction of 7-substituents on the 4,5-epoxy morphinane nucleus, without cleavage of the epoxy bond has been reported by several workers. Bentley et al report in Chem. Comm., JCS C, 57 (1969) that nitrosyl chloride reacts with thebaine in methanol to give the dimethyl ketal of 7-hydroxyiminoneopinone. Reaction of thebane with iodine in the presence of AgNO₂ in methanol-chloroform likewise gives the dimethyl ketal of 7β-iodoneopinone.

Lester et al report in Tetrahedron, 20, 1407 (1964) and 21, 771 (1965) that 14-hydroxy-dihydrocodeinone may be converted to the 7-hydroxyimino derivative by reaction with amylnitrite in chloroform containing ethenolic HCl. This compound can be converted to an ethylene ketal and hydrolyzed to the 7-keto-6-ketal which upon further reaction with dimethylsulphoxonium methylide gives the oxirane.

SUMMARY OF THE INVENTION

The present invention involves 7-methyl, 8β-lower alkyl and 7-methyl-8-lower alkyl substituted B/C cis or trans morphinan-6-one compounds characterized by the structural formula:

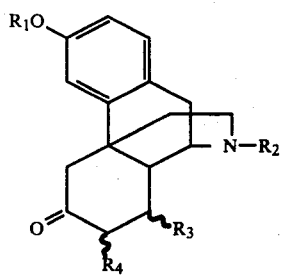

wherein $R_1$ is H or methyl, $R_2$ is cyclopropylmethyl or cyclobutylmethyl, $R_3$ is H, methyl, ethyl or n-propyl and $R_4$ is H or methyl, provided that:

A. when the molecule is in the B/C cis configuration and $R_2$ is cyclobutylmethyl,
  i. $R_3$ is β-methyl, β-ethyl or β-n-propyl when $R_1$ and $R_4$ are H,
  ii. $R_1$ is methyl only when $R_4$ is H and $R_3$ is β-methyl, and
  iii. when $R_4$ is α-methyl, $R_1$ is H and $R_3$ is β-methyl or β-ethyl;

B. when the molecule is in the B/C cis configuration and $R_2$ is cyclopropylmethyl,
  i. $R_3$ is β-methyl and $R_4$ is H or α-methyl when $R_1$ is methyl, and
  ii. $R_3$ is H and $R_4$ is α-methyl when $R_1$ is H; and C. when the molecule is in the B/C trans configuration, $R_1$ is H and $R_2$ is cyclopropylmethyl,
  i. $R_3$ is either α-methyl or H, and
  ii. $R_4$ is β-methyl.

DETAILED DESCRIPTION AND PREFERRED EMBODIMENTS

The compounds of the present invention are useful for the treatment of pain in an individual for whom such therapy is indicated. The term "individual" means a human being or an experimental animal that is a model for a human being. Due to the fact that these compounds exhibit narcotic antagonist activity in addition to their analgesic effect, they can be used for the management of pain without inducing dependence in the individual to whom they are administered. The effective dose of these compounds will vary from individual to individual but may be readily determined by one skilled in the art without undue experimentation. The compounds can be administered by any known conventional method of therapeutic administration such as intravenous, parenteral, buccal, rectal or oral. Dose forms for the administration of these compounds can be prepared by recognized methods in the pharmaceutical sciences.

The synthesis of the compounds of the present invention and their pharmacology is described in the following procedures and examples:

Compounds of Formula I, wherein $R_2$ is cyclopropylmethyl or cyclobutylmethyl, $R_3$ is methyl, ethyl or n-propyl and $R_4$ is H are synthesized by reaction of a first starting material XIII, 7,8-didehydro-3-methoxy-17-methylmorphinan-6-one, a known compound prepared as described by SAWA,

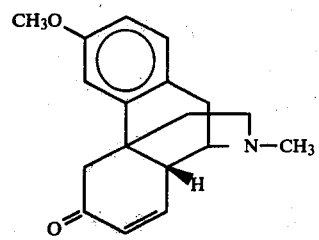

with a lithium diorgano copper reagent, such as lithium dimethyl copper, lithium diethyl copper, or lithium di-n-propyl copper, via a 1,4-addition process. The use of lithium diorgano copper reagents in 1,4-addition processes has been described by Posner (Org. Reactions 19: 1 [1972]). Posner, however, does not teach the use of such reactions in any morphinan system.

The lithium diorgano copper reagent is prepared by the addition of a solution containing about 2 molar equivalents of methyl, ethyl, or n-propyl lithium to a stirred suspension containing about 1 molar equivalent of copper iodide, in a solvent such as ether, tetrahydrofuran or the like, under a moisture-free atmosphere of nitrogen or argon. Lithium dimethyl copper is prepared at 0° C. Lithium diethyl copper and lithium di-n-propyl copper are prepared at −78° C. and allowed to warm to −40° C.

A solution of 7,8-didehydro-3-methoxy-17-methylmorphinan-6-one, XIII in a halogenated hydrocarbon solvent, such as methylene chloride, ethylene chloride, dichloroethane and the like or in an aromatic hydrogen solvent, such as benzene, toluene, xylene and the like, is added to and reacted with the stirred suspension of the lithium diorgano copper reagent preferably under an inert, moisture-free atmosphere. When lithium dimethyl copper is the reagent used, the reaction mixture is preferably maintained at 0° C. during the period of addition of the solution of Compound XIII and the mixture is stirred for up to about 1 hour. When lithium diethyl copper or lithium di-n-propyl copper is the reagent used, the reaction mixture is preferably maintained at about −78° C. to −40° C. during the period of addition of the solution of Compound XIII and during the reaction period of about 10 minutes. The molar ratios of Compound XIII to lithium diorgano copper reagent preferably range from about 1:1 to 1:3, respectively. The use of benzene is preferred in the present process.

The reaction mixture, preferably warmed to about 0° C., is then quenched with an aqueous solution of an ammonium compound, such as ammonium chloride, ammonium hydroxide or the like, preferably in molar excess of the copper contained in the reaction mixture. The resulting mixture is stirred for up to 1 hour to produce an 8-alkylated product having the structural Formula XIV,

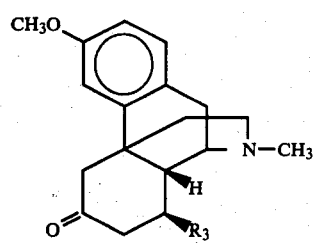

wherein $R_3$ is a methyl, ethyl or n-propyl group.

The aqueous phase of the resultant mixture is separated and adjusted to approximately pH 12 by addition of a strong base, such as 50% sodium or potassium hydroxide. Then, the basic aqueous solution is extracted with a suitable organic solvent, such as ether, chloroform or the like. The organic extract is then washed, dried, and evaporated to isolate the product having structural Formula XIV.

The isolated product XIV is dissolved in a suitable organic solvent such as ether, chloroform or the like, preferably containing a suitable acid acceptor, such as anhydrous potassium carbonate or sodium carbonate or the like. A solution of a cyanogen halide, such as cyanogen bromide, cyanogen chloride, or cyanogen iodide is then gradually added to the mixture with stirring. The suspension is preferably stirred at a temperature from about 20° C. up to the reflux temperature of the solvent for up to 2 hours, to produce a 17-cyano product having the structural Formula XV,

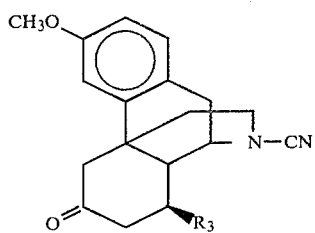

wherein $R_3$ is methyl, ethyl, or n-propyl. The suspension is preferably cooled to a temperature to facilitate separation of insoluble material and the insoluble material is then removed from the suspension by filtration or centrifugation, and the solvent evaporated to isolate the 17-cyano product XV.

The 17-cyano product XV is then hydrolyzed by suspending it in mineral acid, preferably about 1 to 6 N, such as hydrochloric, sulfuric, nitric acid and the like, preferably hydrochloric acid, and preferably heating the mixture at reflux temperature for up to about 8 hours, to produce an 8-alkylated 17-nor product, having the structural Formula XVI,

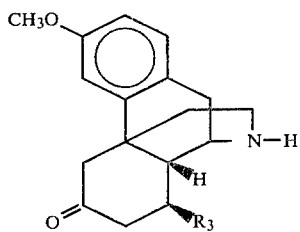

wherein $R_3$ is methyl, ethyl or n-propyl. Compound XV is isolated from the reaction mixture as the hydrochloride salt by evaporation of the solvent.

The 8-alkylated 17-nor product XV or optionally its hydrochloride addition salt is then reacted with an alkylating agent, such as cyclopropylmethyl bromide or cyclobutylmethyl bromide in the presence of an acid acceptor such as potassium or sodium carbonate or bicarbonate. The molar ratios of the 8-alkylated 17-nor product XVI to alkylating agent to acid acceptor preferably range from 1:1:2 to 1:2:4, respectively. The reaction is preferably carried out in a polar organic solvent, such as dimethylformamide, dimethyl sulfoxide, ethanol, or the like, under an inert, moisture-free atmosphere such as nitrogen or argon at a temperature from about 50° C. to 110° C. Dimethylformamide is the most preferred solvent. The resulting product having structure I, wherein $R_1$ is methyl and $R_2$, $R_3$ and $R_4$ are as above, is then isolated by procedures standard to the art, such as solvent extraction or chromatography.

Compounds having Structure I where $R_1$ and $R_4$ are hydrogen are prepared by O-demethylating Compound I, wherein $R_1$ is methyl, using a hydrolytic reagent such as pyridine hydrochloride, hydrobromic acid, or the like. We prefer to use hydrobromic acid, preferably about 48%, at reflux temperature for 10-20 minutes.

When it is desired to have a product with increased water solubility, the organic or inorganic acid addition salts of I can be prepared. Examples of pharmacologically acceptable acid addition salts are the tartrate, hydrochloride, hydrobromide, maleate or the like. We prefer the hydrochloride or hydrobromide salt. The hydrohalide salt is preferably obtained by dissolving the free base in an organic solvent, such as ether or ethyl acetate, and adding gaseous hydrogen chloride or hydrogen bromide thereto or is obtained by dissolving the free base in a lower alcohol, adding aqueous hydrochloric or hydrobromic acid and evaporating the solvents. The pure salts are conveniently obtained by crystallization from such solvents as a lower alcohol including methanol, ethanol or isopropanol or the like, by the addition thereto of a lower ester, such as methyl acetate, ethyl acetate, isopropyl acetate, or the like, followed by removal of the alcohol by boiling.

EXAMPLE I

17-Cyclopropylmethyl-3-Methoxy-8β-Methylmorphinan-6-one (TR-5119).

This example includes the preparation of intermediates to the title compound.

A. 8β,17-Dimethyl-3-methoxymorphinan-6-one (TR-5068)

I. Preparation in ether-benzene.

A solution of lithium dimethyl copper was prepared at 0° C. under an argon atmosphere by adding methyl lithium (0.159 mole, 86 ml of a 1.84 M solution in ether; available from Alfa Chem. Co.) to a suspension of copper iodide (15.1 g, 0.0794 mole) in anhydrous ether. To this solution was added, in a dropwise manner, a solution of 7,8-didehydro-3-methoxy-17-methylmorphinan-6-one (18.0 g, 0.064 mole; prepared as described by SAWA) in dry benzene and the resulting mixture was stirred at about 0° C. for 1 hour. This mixture was then poured into saturated NH₄Cl solution (1 L) and stirred at room temperature for about 30 minutes. The organic phase was separated from the mixture and the aqueous phase was adjusted to about pH 12 by the addition of 50% NaOH solution. The resulting aqueous phase was then extracted with three portions of chloroform, and the combined organic extracts were back-washed with saturated NH₄Cl solution, dried over MgSO₄, and evaporated. The resulting residue was dissolved in ethyl acetate and the solvent was evaporated to give a crystalline residue. The crystalline residue was recrystallized from ethyl acetate after charcoal treatment to give 10.0 g of TR-5068, mp 126°-127° C. An additional 3.0 g of product were obtained from the mother liquor to give an overall yield of 68%. Recrystallization from ethanol gave pure TR-5068, mp 131°-132° C.

Anal. Calcd. for C$_{19}$H$_{25}$NO$_2$: C, 76.22; H, 8.42; N, 4.68. Found: C, 76.16; H, 8.35; N, 4.49.

The hydrochloride of TR-5068 was prepared by dissolving the free base in ethanol, adding excess concentrated HCl, and evaporating the mixture to dryness. The resulting residue was further dried by azeotropic means first with ethanol, then with 1:1 V/V ethanol: benzene, and then with benzene. The dried product was crystallized from ethanol-ethyl acetate to give TR-5068. HCl, mp 274°–276° C.

Anal. Calcd. for C$_{19}$H$_{25}$NO$_2$.HCl: C, 67.94; H, 71.80; N, 4.17. Found: C, 68.35; H, 7.83; N, 4.01.

II. Preparation in ether-methylene chloride

A solution of lithium dimethyl copper, prepared from methyl lithium (0.131 mole) and copper iodide (12.4 g, 0.066 mole) as described in Example 1A, was prepared at 0° C. under argon. To this solution there was added, dropwise, a solution of 7,8-didehydro-3-methoxy-17-methylmorphinan-6-one (15.0 g, 0.053 mole; prepared according to SAWA) in 150 ml of methylene chloride. The reaction was further treated as in Example 1. The residue obtained upon evaporation of the chloroform extract was crystallized from ethyl acetate to give 9.70 g of TR-5068 (61% yield).

B. 17-Cyano-3-methoxy-8β-methylmorphinan-6-one.

A rapidly stirred mixture of 8β,17-dimethyl-3-methoxymorphinan-6-one (free base; prepared in Part A) in chloroform (1.0 g/10 ml) containing 1.5 g finely powdered dry K$_2$CO$_3$ was treated dropwise with a solution of cyanogen bromide in chloroform (1.2 equivalents; 1.0 g/20 ml). The mixture was stirred rapidly for 30 minutes and then heated at reflux for an additional two hours. The solution was cooled, filtered, evaporated to dryness and azeotroped with alcohol. The crystalline, mp. 202°–205° C., product was obtained in 81% yield and was used without further pruification.

C. 3-Methoxy-8β-methylmorphinan-6-one Hydrochloride.

A suspension of 17-cyano-3-methoxy-8β-methylmorphinan-6-one (prepared in Part B) in 2 N HCl (1 g/30 ml) was refluxed for 8 hours. The resulting solution was evaporated to dryness, azeotroped several times with ethanol, and the crystalline residue suspended in ethanol and collected. The product was used without further purification. The yield of crystalline material, mp 204°–208° C., was 90%.

D. 17-Cylopropylmethyl-3-methoxy-8β-methylmorphinan-6-one (TR-5119).

To a suspension of 3-methoxy-8β-methylmorphinan-6-one hydrochloride (prepared in Part C) in DMF (1 g/10 ml) was added NaHCO$_3$ (2.2 equivalents [eq]) and cyclopropylmethyl bromide (1.5 eq). The mixture was heated under an argon atmosphere at 100° C. for 16 hours, then cooled. The mixture was filtered and the filtrate was evaporated in high vacuum to yield a residue. The residue was dissolved in water, adjusted to about pH 11 with concentrated NH$_4$OH and extracted with three portions of benzene. The organic phase was dried, filtered and evaporated to a residue. The residue was chromatographed over silica Gel G using 15:1 (V/V) chloroform:methanol as the eluant. Pure chromatographic fractions were combined and the product crystallized as the free base, mp 114°–115° C., in 72% yield.

Anal. Calcd. for C$_{22}$H$_{29}$NO$_2$: C, 77.84; H, 8.61; N, 4.13. Found: C, 77.75; H, 8.33; N, 4.00.

EXAMPLE 2

17-Cyclobutylmethyl-3-methoxy-8β-methylmorphinan-6-one Hydrochloride (TR-5132).

A sample of 3-methoxy-8β-methylmorphinan-6-one hydrochloride (prepared in Example 1C) was treated as in Example 1D, except that cyclobutylmethyl bromide (1.5 eq) was substituted for the cyclopropylmethyl bromide. The product was isolated as in Example 1D and converted to the hydrochloride salt, yield 34%, mp 217°–220° C.

Anal. Calcd. for C$_{23}$H$_{31}$NO$_2$.HCl: C, 70.84; H, 8.27; N, 3.59; Cl, 9.50 Found: C, 70.47; H, 8.19; N, 3.48; Cl, 9.23.

EXAMPLE 3

17-Cyclobutylmethyl-3-hydroxy-8β-methylmorphinan-6-one Hydrochloride (TR-5130).

A sample of 17-cyclobutylmethyl-3-methoxy-8β-methylmorphinan-6-one (prepared in Example 2) and 48% aqueous HBr (1.0 g/5 ml, respectively) was refluxed for 20 minutes in a pre-heated oil bath at 140° C. The mixture was cooled in ice and diluted with 30 ml of water. The aqueous solution was adjusted to about pH 11 by addition of concentrated NH$_4$OH. The basic mixture was extracted with three portions of chloroform, and the organic extract was treated as in Example 1D. The residue was chromatographed over Silica Gel G as in Example 1D and the product was isolated as in the HCl salt, yield 84%, mp 150° C. dec, with foaming. The tartaric acid salt of 17-cyclobutylmethyl-3-hydroxy-8β-methylmorphinan-6-one can be prepared by procedures apparent to those skilled in the art.

Anal. Calcd. for C$_{22}$H$_{29}$NO$_2$.HCl: C, 70.29; H, 8.04; N, 3.73; Cl, 9.43. Found: C, 70.13; H, 7.79; N, 3.57; Cl, 9.25.

EXAMPLE 4

Preparation of 17-Cyclobutylmethyl-8β-ethyl-3-hydroxy morphinan-6-one Hydrochloride (TR-5200).

This example includes the preparation of intermediates to the title compound.

A. 8β-Ethyl-3 methoxy-17-methylmorphinan-6-one Hydrochloride (TR-5174)

Ethyl lithium was prepared by the dropwise addition of ethyl chloride (3.1 ml, 42 mmol) in 20 ml of ether under argon to finely dispersed lithium (86 mmol, 0.60 g) in 30 ml of ether at 0° C. with stirring for about 20 minutes. After cooling the mixture to −78° C., the resulting suspension was transferred by the use of argon pressure, to a suspension of CuI (4.00 g, 21 mmol) in 200 ml of ether stirred at about −78° C. The suspension was allowed to warm to about −40° C. and maintained at this temperature for 10 minutes. A solution of 7,8-didehydro-3-methoxy-17-methylmorphinan-6-one (4.77 g, 16.8 mmol) in benzene (50 ml) was then added rapidly to the suspension dropwise, while maintaining the temperature at about −40° C. and stirring for 10 minutes. The resulting mixture was allowed to warm to 0° C. This reaction mixture was treated with saturated NH$_4$Cl solution (300 ml) and the product was extracted with chloroform as described in Example 1. The free base of TR-5174, 5.5 g, was obtained as a syrup. The product was converted to the HCl salt as described in Example 1A and crystallized from methanol-ethyl acetate to give 4.22 g (71%) of TR-5174, mp 257° C. dec. Recrystallization from the same solvent pair gave pure TR-5174, mp 263°–265° C.

Anal. Calcd. for $C_{20}H_{27}NO_2 \cdot HCl$: C, 68.65; H, 8.07; N, 4.00; Found: C, 68.76; H, 8.02; N, 3.70.

B. 17-Cyano-8β-ethyl-3-methoxymorphinan-6-one.

To a rapidly stirred solution of 8β-ethyl-3-methoxy-17-methylmorphinan-6-one (prepared in Part A) was added cyanogen bromide as in Example 1B. The product, mp. 141°–145° C., was obtained in 73% yield.

C. 8β-Ethyl-3-methoxymorphinan-6-one Hydrochloride.

A sample of 17-cyano-8β-ethyl-3-methoxymorphinan-6-one was treated with 2 N HCl as described in Example 1C. The product was isolated in 72% yield, mp 280° C.

D. 17-Cyclobutylmethyl-8β-ethyl-3-methoxymorphinan-6-one Hydrochloride (TR-5192).

A sample of 8β-ethyl-3-methoxymorphinan-6-one hydrochloride prepared in Part C, was treated as in Example 2. The yield as HCl salt, mp. 252°–254° C., was 77%.

Anal. Calcd. for $C_{24}H_{33}NO_2 \cdot HCl$: C, 71.35; H, 8.48; N, 3.47. Found: C, 71.08; H, 8.32; N, 3.25.

E. 17-Cyclobutylmethyl-8β-ethyl-3-hydroxy-morphinan-6-one Hydrochloride (TR-5200).

A sample of 17-cyclobutylmethyl-8β-ethyl-3-methoxymorphinan-6-one, prepared in Part D, was treated as described in Example 3. The product was obtained as the HCl salt, yield 98%, mp 190° C. dec. with foaming.

Anal. Calcd. for $C_{23}H_{31}NO_2 \cdot HCl \cdot 0.5\ C_2H_5OH$: C, 69.86; H, 8.53; N, 3.40. Found: C, 69.84; H, 8.53; N, 3.23.

EXAMPLE 5

Preparation of 17-cyclobutylmethyl-3-hydroxy-8β-n-propylmorphinan-6-one Hydrochloride (TR-5204).

This example includes the preparation of intermediates to the title compound.

A. 3-Methoxy-17-methyl-8β-n-propylmorphinan-6-one Hydrochloride (TR-5175)

n-Propyl lithium was prepared from propyl chloride (42 mmol) and metallic lithium (86 mmol) and then added to CuI (21 mmol) in ether at −78° C. (c.f. Example 4A) to produce the lithium di-n-propyl copper reagent. This compound was reacted with 7,8-didehydro-3-methoxy-17-methylmorphinan-6-one (16.8 mmol). The product (TR-5175) was isolated as in Example 1A as a syrup which crystallized on standing. This syrup was converted to the HCl salt and crystallized from methanol-ethyl acetate to give 4.28 g (70%) of TR-5175.HCl, mp 234°–235° C. Recrystallization gave the pure TR-5175.HCl, mp 235°–237° C.

Anal. Calcd. for $C_{21}H_{29}NO_2 \cdot HCl$: C, 69.31; H, 8.31; N, 3.85. Found: C, 69.70; H, 8.42; N, 3.86.

B. 17-Cyano-3-methoxy-8β-n-propylmorphinan-6-one.

To a rapidly stirred solution of 3-methoxy-17-methyl-8β-n-propylmorphinan-6-one (prepared in Part A) was added cyanogen bromide as in Example 1B. The product was obtained as a syrup, 97% yield, and was used without further purification.

C. 3-Methoxy-8β-n-propylmorphinan-6-one Hydrochloride.

A sample of 17-cyano-3-methoxy-8β-n-propylmorphinan-6-one was treated as described in Example 1C. The product, mp. >280° C., was isolated in 57% yield.

D. 17-Cyclobutylmethyl-3-methoxy-8β-n-propylmorphinan-6-one Hydrochloride (TR-5197)

A sample of 3-methoxy-8β-n-propylmorphinan-6-one hydrochloride prepared in Part C, was treated as in Example 2. The yield as HCl salt was 46%, mp 192°–193° C.

Anal. Calcd. for $C_{25}H_{35}NO_2 \cdot HCl$: C, 71.83; H, 8.68; N, 3.35. Found: C, 71.45; H, 8.39; N, 3.20.

E. 17-Cyclobutylmethyl-3-hydroxy-8β-n-propylmorphinan-6-one Hydrochloride (TR-5204)

A sample of 17-cyclobutylmethyl-3-methoxy-8β-n-propylmorphinan-6-one, prepared in Part D, was treated as in Example 3. The product was obtained as the HCl salt, yield 99%, mp 210°–212° C.

Anal. Calcd. for $C_{24}H_{32}NO_2 \cdot HCl$: C, 71.35; H, 8.48; N, 3.47. Found: C, 71.33; H, 8.38; N, 3.26.

EXAMPLE 6

Preparation of Reference Compounds

I. 17-Cyclobutylmethyl-3-methoxymorphinan-6-one Hydrochloride (TR-5148).

A. 3-Methoxy-17-methylmorphinan-6-one.

A 2.0 g sample of 7,8-didehydro-3-methoxy-17-methylmorphinan-6-one (prepared as described by SAWA et al., Tetrahedron 20: 2247 [1964]) was dissolved in 300 ml of 95% ethanol and hydrogenated at 50 psi for 4 hours using 150 mg of 10% Pd/C catalyst. The solution was filtered and evaporated to yield a crystalline residue. The product was recrystallized from ethanol to give 760 mg of product, mp 187°–188.5° C. (lit. mp 188°–189° C.).

Anal. Calcd. for $C_{18}H_{23}NO_2$: C, 75.76; H, 8.12; N, 4.91. Found: C, 75.58; H, 7.95; N, 4.79.

B. 17-Cyano-3-methoxymorphinan-6-one.

An 8.4 g sample of 3-methoxy-17-methylmorphinan-6-one (prepared as in Part 6A) in 85 ml of chloroform containing 6.09 g of dry $K_2CO_3$ was reacted with 3.8 g of cyanogen bromide and the product isolated as described in Example 1B. The product was crystallized from ethanol; yield 6.96 g (80%), mp 211°–214° C.

C. 3-Methoxymorphinan-6-one Hydrochloride.

A suspension of 17-cyano-3-methoxymorphinan-6-one (6.9 g; prepared in Part B) in 200 ml of 2 N HCl was refluxed for 8 hours. The resulting solution was treated as in Example 1C to yield 5.2 g of crystalline product, mp 190°–200° C. An additional 0.9 g was obtained from the mother liquor. Total yield was 6.1 g (85%).

D. 17-Cyclobutylmethyl-3-methoxymorphinan-6-one Hydrochloride (TR-5148).

A sample of 3-methoxymorphinan-6-one hydrochloride (3.5 g, 0.011 mole; prepared in Part C) was treated with 2.56 g (0.017 mole) of cyclobutylmethyl bromide, and the product (2.4 g) was isolated as in Example 2. The product was converted to the hydrochloride salt as described in Example 1A, and recrystallized from methanol-ethyl acetate to yield 1.4 g of TR-5148, mp 272°–274° C., dec.

Anal. Calcd. for $C_{22}H_{29}NO_2 \cdot HCl$: C, 70.29; H, 8.04; N, 3.73; Cl, 9.43. Found: C, 70.16; H, 7.86; N, 3.66; Cl, 9.50.

II. 17-Cyclobutylmethyl-3-hydroxymorphinan-6-one Hydrochloride (TR-5153).

A sample of TR-5148 (1.0 g; prepared in Part ID) was reacted with hydrobromic acid and the product isolated as in Example 3. The yield of product was 782 mg. After conversion to the HCl salt the product was crystallized from methanol-ethyl acetate to yield 420 mg of TR TR-5153, mp 262°–264° C. dec.

Anal. Calcd. for $C_{21}H_{27}NO_2 \cdot HCl$: C, 69.69; H, 7.80; N, 3.87; Cl, 9.80. Found: C, 69.41; H, 7.90; N, 3.91; Cl, 9.91.

III. 17-Cyclopropylmethyl-3-methoxymorphinan-6-one Hydrochloride (TR-5152).

A sample of 3-methoxymorphinan-6-one hydrochloride (3.08 g, 10 mmol, prepared in Part IC), was reacted with cyclopropylmethyl bromide in the presence of sodium bicarbonate as described in Example 1D. After chromatography on Silica Gel G using 20:1 V/V chloroform-methanol, 2.5 g of the desired product was isolated as a syrup. This was converted to the hydrochoride salt to yield 2.1 g (58%) of TR-5152, mp 265°–267° C.

Anal. Calcd. for $C_{21}H_{27}N_2 \cdot HCl$ C, 66.69; H, 7.80; N, 3.87; Cl, 9.80. Found: C, 66.83; H, 7.82; N, 3.74; Cl, 9.83

IV. 17-Cyclopropylmethyl-3-hydroxy morphinan-6-one (TR-5160).

A sample of TR-5152, prepared in part III, was treated with refluxing hydrobromic acid and the products isolated as in Example 3. The title compound was obtained in 64% yield after chromatography and crystallized from water to give pure TR-5160, mp. 125°–127° C.

Anal. Calcd. for $C_{20}H_{25}NO_2$: C, 77.14; H, 8.09; N, 4.50. Found: C, 76.94; H, 8.36; N, 4.44

This compound has been reported by Y. Sawa, R. Maeda and H. Tada as the monohydrate, mp. 127°–128° (U.S. Pat. No. 3,654,280, Apr. 4, 1972, Example 6).

V. 17-Cyclopropylmethyl-3-hydroxy-isomorphinan-6-one Hydrochloride (TR-5222).

A. 3-Methoxy-17-methyl-isomorphinan-6-one (TR-5193).

A solution of 7,8-didehydro-3-methoxy-17-methylisomorphinan-6-one (10.0 g, prepared according to Y. Sawa and S. Maeda, Tetrahedron, 20, 2247, 1964) in aqueous ethanol (300 ml) was hydrogenated at an initial pressure Removal of the catalyst by filtration was followed by evaporation of the filtrate to a syrup which crystallized on trituration with ethanol. The crystals (6.7 g) were collected and recrystallized from ethanol to give pure TR-5193, mp. 91°–92°.

Anal. Calcd for $C_{18}H_{23}NO_2$: C, 75.76; H, 8.12; N, 4.91 Found: C, 75.84; H, 8.06; N, 4.74

B. 17-Cyano-3-methoxy-isomorphinan-6-one.

This compound was prepared as described in experiment 6IB. The desired product was obtained as crystals, mp. 178°–180°, in 66% yield.

C. 3-Methoxy-isomorphinan-6-one Hydrochloride.

This compound was prepared by the hydrolysis of the 17-cyano compound in he usual fashion using 2 N HCl to give the desired product as crystals, mp. 265°–267° C., in 67% yield.

D. 17-Cyclopropylmethyl-3-methoxy-isomorphinan-6-one Hydrochloride (TR-5203).

This compound was prepared in a manner analogous to that described above in Experiment 6ID except using cyclopropylmethyl bromide. The crude product was chromatographed to give a 70% yield of the free base of TR-5203. This was converted to the hydrochloride which crystallized from methanol-ethyl acetate to give hygroscopic TR-5203 as the monohydrate, mp. 255°–256° C.

Anal. Calcd. for $C_{21}H_{27}NO_2 \cdot HCl \cdot H_2O$: C, 66.38; H, 7.96; N, 3.69 Found: C, 66.40; H, 7.75; N, 3.68

E. 17-Cyclobutylmethyl-3-methoxy-isomorphinan-6-one (TR-5202).

This compound was prepared in a manner analogous to that described in experiment 6ID. The crude product was purified to give a 50% yield of TR-5202 which crystallized from ethanol to give needles, mp. 96.5°–97.5°.

Anal. Calcd. for $C_{22}H_{29}NO_2$: C, 77.84; H, 8.61; N, 4.13 Found: C, 77.79; H, 8.69; N, 3.95

F. 17-Cyclopropylmethyl-3-hydroxy-isomorphinan-6-one Hydrochloride (TR-5222).

This compound was prepared as described in Example 3 from TR-5203 by refluxing with 48% HBr. After workup, the residue was chromatographed (10:1 chloroform-methanol with 1% concentrated ammonia) to give a 48% yield of the free base of TR-5222 as a foam. The foam was converted to the HCl salt, mp. >265° C., which crystallized from ethyl acetate.

Anal. Calcd. for $C_{20}H_{25}NO_2 \cdot HCl$: C, 69.05; H, 7.53; N, 4.03 Found: C, 68.47; H, 7.63; N, 3.86

VI. 17-Cyclobutylmethyl-3-hydroxy-isomorphinan-6-one Hydrochloride (TR-5223).

This compound was prepared in a manner analogous to that described in Example 3 from the 3-methoxy compound, TR-5202, by refluxing with 48% HBr. After workup, the residue was chromatographed to give an 87% yield of the free base. The HCl salt, mp. >265°, was obtained in crystalline form from methanol-ethyl acetate.

Anal. Calc. for $C_{21}H_{27}NO_2 \cdot HCl$: C, 69.69; H, 7.80; N. 3.87 Found: C, 69.73; H, 7.87; N, 3.82

The preparation of those compounds corresponding to Formula I wherein R4 is methyl and R3 is either H or lower aklyl is schematically set out in Scheme I. The numbering of the compounds of Scheme I corresponds to the detailed experimental portion set out in Examples 7 and 8. Compounds shown in Scheme I are synthesized by reaction of the first starting mateial thebaine (1), a naturally occuring opium alkaloid, with lithium dimethyl cuprate. The lithium dimethyl copper reagent is prepared as described, supra, at about 0° C. A solution of thebaine (1) in a halogenated hydrocarbon or aromatic hydrocarbon solvent is reacted with the lithium dimethyl cuprate as before. The reaction mixture is quenched and processed in a similar manner. The product, 3,6-dimethoxy-7β,17-dimethyl-4-hydroxy-5,6,8,14-tetahydro-morphinane, 2, is isolated as the crystalline chloroform solvate. This is converted to the 4-phenyl ether by reaction with bromobenzene in refluxing pyridine in the presence of an acid acceptor and copper powder. The 4-phenoxy group is cleaved from 3 to give 4 by use of sodium in a liquid ammonia-toluene mixture.

Acid hydrolysis of 4 by use of 25% HCl at 100° C. for one hour gives a mixture of the isomeric $\alpha,\beta$-unsaturated ketones 5 and 6 which are most conveniently separated at this stage by chromotography. Each isomer is then individually carried through the remainder of the reaction sequence.

The double bond in the 7,8 position of 5 and 6 is reduced by treatment with hydrogen over a palladium-charcoal catalyst in acidified ethanol solution to give compounds 7 and 24. In the B/C cis series, the hydrogen is added from the $\beta$ face of the molecule with the result that the 7-methyl group in 7 occupies the $\alpha$ position. In the B/C trans series we believe that the methyl group occupies the $\beta$ position.

Alternatively, 5 or 6 may be alkylated in a 1,4-manner using methods described supra by use of lithium dimethyl copper at 0° C., or by use of lithium divinyl copper at about −40°, to give 7-methyl-8-alkylated-morphinan-6-ones. The 8-vinyl compound is not isolated but is reduced by catalytic hydrogenation to an ethyl group. Using methods outlined, supra, the 17-methyl group is removed and a cycloalkylmethyl moiety introduced at this position.

SCHEME I

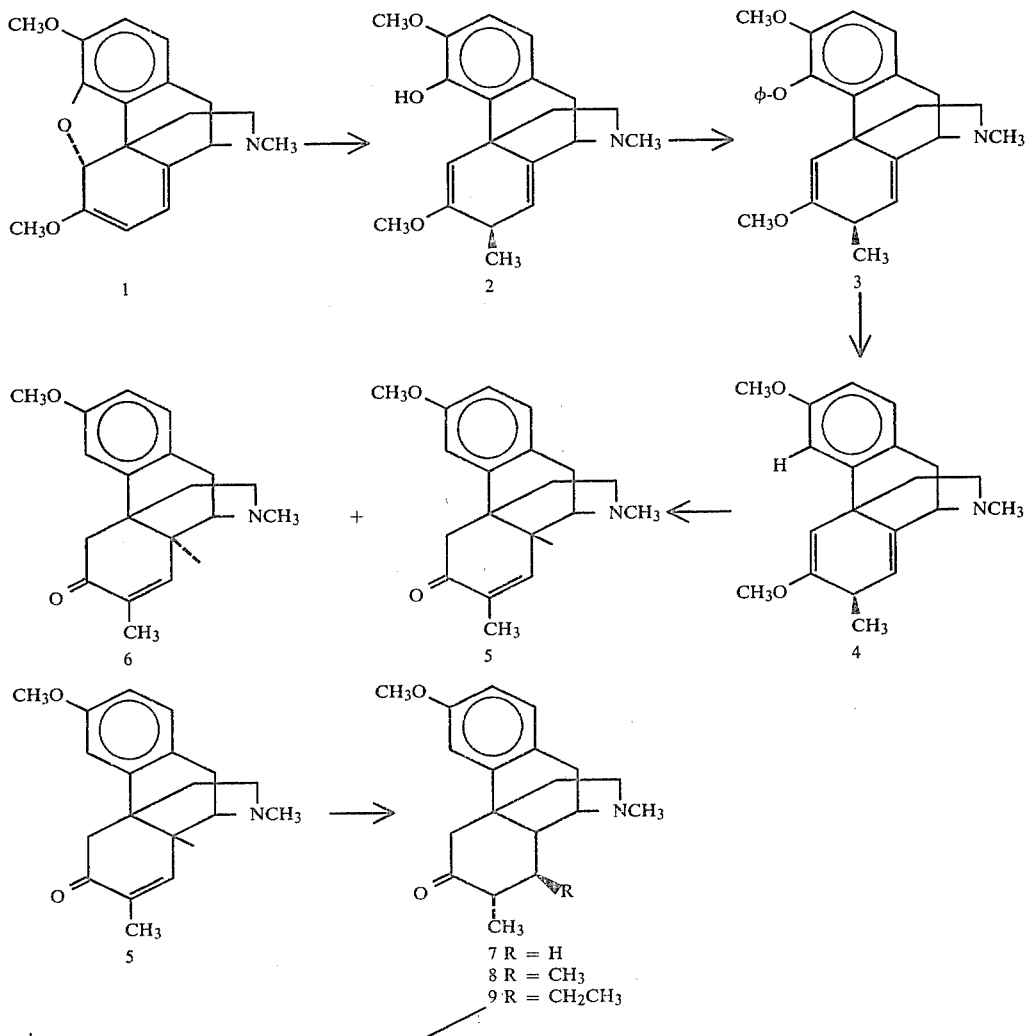

-continued
SCHEME I
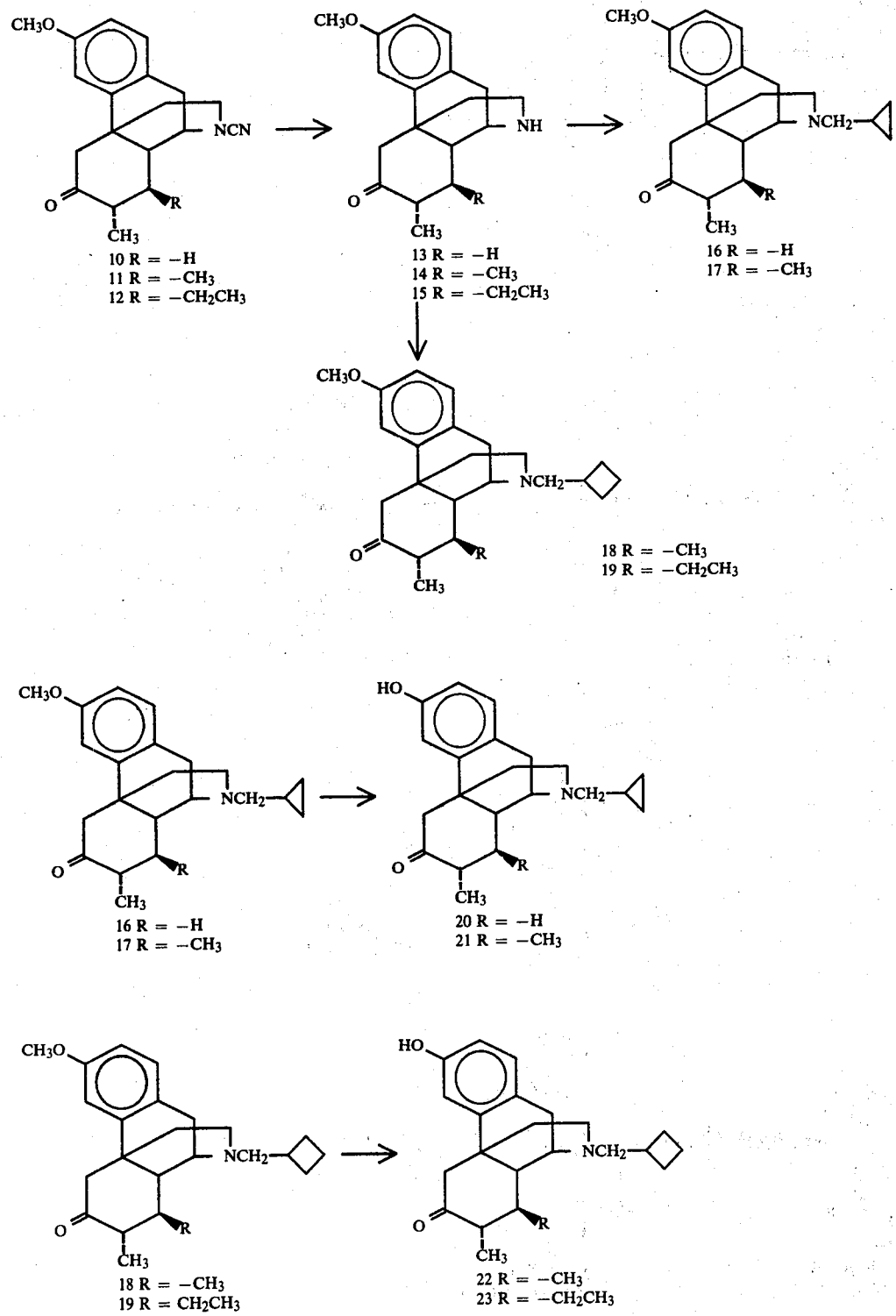

SCHEME I
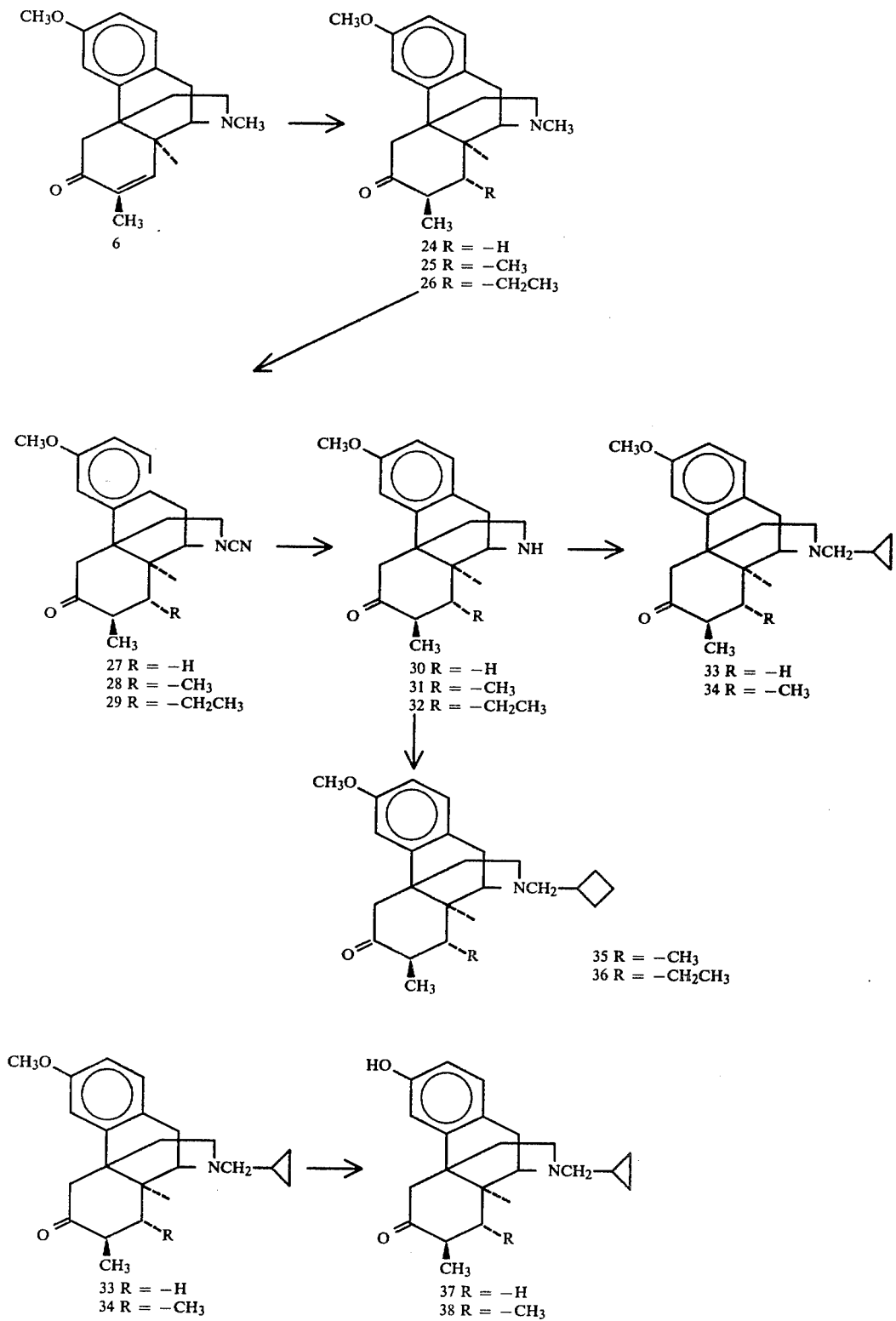

-continued
SCHEME I

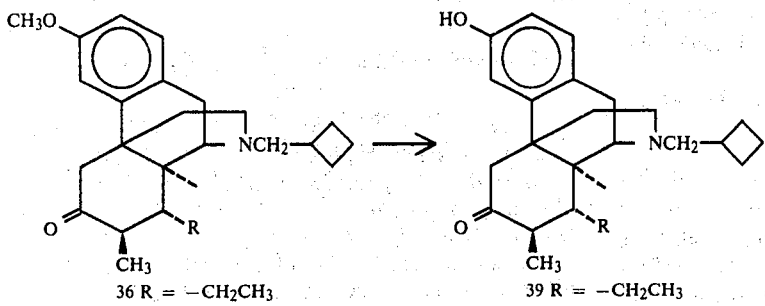

36 R = —CH$_2$CH$_3$  
39 R = —CH$_2$CH$_3$

EXAMPLE 7

Preparation of 17-Cyclopropylmethyl and Cyclobutylmethyl-7α-Methyl-8-Unsubstituted and 8β-Alkyl-Morphinan-6-Ones

A.

3,6-Dimethoxy-7β,17-dimethyl-4-hydroxy-5,6,8,14-tetradehydromorphinane (2).

To a solution of lithium dimethyl cuprate in ether (500 ml), prepared from copper iodide (23.81 g, 125 mmol) and methyl lithium (250 mmol, 136 ml of a 1.8 M solution in ether containing lithium bromide), stirred in an ice-salt bath under an argon atmosphere was added rapidly in a thin stream a solution of thebaine (1, 31.14 g, 100 mmol) in benzene (500 ml). The resulting suspension was stirred for 1 hr. in the cold, then poured into saturated NH$_4$Cl solution (600 ml) and the mixture stirred for 15 min. The organic layer was separated, and the aqueous phase adjusted to pH 13–14 by use of 50% NaOH. The aqueous phase was then extracted with two portions of chloroform, the combined organic phases washed with dilute NH$_4$OH and dried. Evaporation gave a foam which crystallized from chloroform with the addition of hexane to give 33.20 g (74%) of 2 as the mono-chloroform solvate, mp. 97°–100°. Recrystallization from the same solvent pair gave analytically pure 2.CHCl$_3$, mp. 98°–101.5°. IR (CDCl$_3$): 3500 cm$^{-1}$ (OH). NMR (CDCl$_3$):δ7.30, s (1), CHCl$_3$; 6.65, m(2), H1 and H2; 6.13 s(1), H5α; 5.47, d(1), H8, J$_{7,8}$=3 Hz; 3.86, s(3), 3—OCH$_3$; 3.63, s(3), 6—OCH$_3$; 2.33, s(3), 17—NCH$_3$; 1.17, d(3), 7—CH$_3$, J$_{7H,7CH3}$=7 Hz; exchangeable, 4—OH at ~6.20.

Anal. Calcd. for C$_{20}$H$_{25}$NO$_3$.CHCl$_3$: C, 56.45; H, 5.87; N, 3.13. Found: C, 56.27; H, 5.82; N, 3.07.

B.

3,6-Dimethoxy-7β,17-dimethyl-4-phenoxy-5,6,8,14-tetradehydromorphinane (3).

Compound 2 (18.80 g, 42 mmol) was dried by azeotropic distillation several times with pyridine and then dissolved in pyridine (100 ml). To this solution was added bromobenzene (4.90 ml, 46 mmol), powdered potassium carbonate (6.40 g, 46 mmol) and 40μ copper powder (1.34 g, 21 mmol) and the resulting mixture refluxed under argon for 48 hours. The solution was filtered while hot, the insoluble material washed with warm pyridine and the filtrate evaporated to dryness. The residue was dissolved in benzene, treated with charcoal and evaporated to a crystalline residue. Crystallization from ethyl acetate gave 14.33 g (85%) of 3 as tan needles, mp 177°–178°. Recrystallization from ethyl acetate gave analytically pure 3, mp. 177°–178°. NMR (CDCl$_3$): δ7.43-6.67, m(7), aromatic; 5.57, m(2), H5α and H8; 3.60, 3—OCH$_3$; 3.03; 6—OCH$_3$; 2.42, N—CH$_3$; 1.17, d(3), 7—CH$_3$, J=7 Hz.

Anal. Calcd. for C$_{26}$H$_{29}$NO$_3$: C, 77.39; H, 7.24; N, 3.47. Found: C, 77.27; H, 7.16; N, 3.32.

C.

3,6-Dimethoxy-7β,17-dimethyl-5,6,8,14-tetradehydromorphinane (4).

To liquid ammonia (500 ml) at −78° was added dropwise a solution of 3 (17.20 g, 43 mmol) in toluene (150 ml). To the stirred biphasic system was added sodium (2.94 g, 0.128 g atoms) and the resulting blue solution stirred at −78° for 1 hr. Excess NH$_4$Cl was added to quench the blue color and the ammonia allowed to evaporate at room temperature. The residual suspension was diluted with 5% NaOH and extracted 3 times with ether. Evaporation of the dried organic phase gave 4 as a tan syrup. NMR (CDCl$_3$): δ7.17-6.53; m(3), aromatic; 5.47, d(1), H8, J$_{7,8}$=4 Hz; 5.10, s(1), H5α; 3.78, 3.65, 2.43, singlets; 1.23 d(3), 7—CH$_3$, J=7 Hz.

D.

7,8-Didehydro-7,17-dimethyl-3-methoxymorphinan-6-one (5) and
7,8-Didehydro-7,17-dimethyl-3-methoxy-isomorphinan-6-one (6).

A solution of 4 (2.70 g) in 25% HCl (15 ml) was heated at 90°–110° (pre-heated oil bath) for 1 hr. The cooled solution was made basic by the addition of concentrated NH$_4$OH and extracted 3 times with chloroform. The chloroform extracts were evaporated to give a foam which was chromatographed over Silica Gel G using 10:1 chloroform-methanol. The first major fraction gave 0.89 g (35%) of crystalline material which was recrystallized from ether-ethyl acetate to give pure 5, mp 118.5°–120°. NMR (CDCl$_3$): δ7.27-6.67, m(4), aromatic and H8; 3.80, 2.40, singlet; 1.90, m(3), 7—CH$_3$.

Anal. Calcd. for C$_{19}$H$_{23}$NO$_2$: C, 76.74; H, 7.80, N, 4.71. Found: C, 76.76; H, 7.68; N, 4.62.

The second major fraction gave 0.93 g (36%) of 6 which was recrystallized from ethyl acetate to give an analytical sample of 6, mp 148°–150°. NMR (CDCl$_3$): δ7.11-6.32 (4H); 3.75, 2.45, singlets; 1.58, m(3), 7—CH$_3$.

Anal. Found: C, 76.78; H, 7.66; N, 4.52.

E. 7α,17-Dimethyl-3-methoxymorphinan-6-one(7).

Compound 5 (10.0 g) was hydrogenated at an initial pressure of 50 psi over 10% palladium on charcoal (1.0 g) in 95% ethanol (250 ml) containing concentrated HCl (0.5 ml) for 3 hr. After removal of the catalyst, the filtrate was evaporated to a small volume and partitioned between dilute NH$_4$OH and chloroform. Evaporation of the chloroform gave a crystalline residue which was recrystallized from ethyl acetate-ether to give 6.90 g (69%) of pure 7, mp 148.5°–150°. NMR (CDCl$_3$): δ7.20–6.57, aromatic; 3.82, 2.43, singlets; 0.87, d(3), 7—CH$_3$, J=7 Hz.

Anal. Calcd. for C$_{19}$H$_{25}$NO$_2$: C, 76.22; H, 8.42; N, 4.68. Found: C, 76.36; H, 8.45; N, 4.65.

F. 3-Methoxy-7α,8β,17-trimethylmorphinan-6-one (8).

To a solution of lithium dimethyl cuprate (63 mmol) prepared in ether (400 ml), under argon at ice-salt bath temperature as described in 2 above, was added 5 (15.00 g, 50 mmol) in warm benzene (350 ml) rapidly in a thin stream. The cooling bath was removed and the reaction mixture stirred at ambient temperature for 1 hr. Workup as described above gave a residue which was crystallized from ether-ethyl acetate to give 5.83 g of 8. Chromatography of the mother liquors gave an additional 7.29 g (83% overall yield) of crystalline 8. Recrystallization from ether gave analytically pure 8, mp 101°–102°. NMR (CDCl$_3$): δ7.07–6.15, aromatic; 3.77, 2.47, singlets; 1.08, unsymmetrical d(3), 8—CH$_3$; 0.88 d(3), 7—CH$_3$.

Anal. Calcd. for C$_{20}$H$_{27}$NO$_2$: C, 76.64; H, 8.68; N, 4.47. Found: C, 76.58; H, 8.54; N, 4.34.

G. 7α,17-Dimethyl-8β-ethylmorphinan-6-one Hydrochloride (9).

Vinyl lithium was prepared at −78° under argon by stirring vinyl bromide (3.0 ml, 42 mmol) with t-butyllithium (63 ml of a 1.35 M solution in pentane) for 1 hour. The resulting suspension was transferred to a suspension of copper iodide (4.00 g, 21 mmol) in ether (100 ml) kept at −78°. The mixture was allowed to warm to −40° and while maintaining this temperature, a solution of 5 (5.00 g, 17 mmol) in methylene chloride (100 ml) was added rapidly dropwise. After stirring for 15 min at −40°, the mixture was allowed to warm to 20° and further processed as described for 2 above. Evaporation gave a residue which showed 2 major spots by thin layer chromatography for the 1,2- and 1,4-addition products. The residue was dissolved in 95% ethanol (250 ml), concentrated HCl (0.5 ml) and 10% palladium on charcoal (1.0 g) added and the mixture hydrogenated at 50 psi for 4 hr. After removal of the catalyst, the filtrate was evaporated to a small volume and partitioned between dilute NH$_4$OH and chloroform. The chloroform solution was evaporated to dryness and the residue chromatographed over Silica Gel G (750 g) using 15:1 chloroform-methanol containing 0.5% concentrated NH$_4$OH as the eluant. Fractions containing the desired 1,4 product were pooled to give 2.29 g of 9 as a glass. NMR (CDCl$_3$): δ7.07–6.53, aromatic; 3.78, 2.50, singlets, 1.43–0.70, m(6H), 7—CH$_3$ and 8—CH$_2$CH$_3$. The glass was converted to 9.HCl which was obtained as a foam for analysis.

Anal. Calcd. for C$_{21}$H$_{29}$NO$_2$.HCl: C, 69.31; H, 8.31; N, 3.85. Found: C, 69.15; H, 8.11; N, 3.59.

H. 17-Cyano-3-methoxy-7α-methylmorphinan-6-one (10).

To a mixture of 7 (9.90 g, 33 mmol) and potassium carbonate (6.86 g, 50 mmol) in chloroform (75 ml) was added dropwise a solution of cyanogen bromide (4.30 g, 40 mmol) in chloroform (50 ml). Upon completion of the addition, the mixture was refluxed for 90 minutes. The cooled suspension was filtered and the filtrate evaporated to dryness and azeotroped with ethanol to give 7.24 g (71%) of crystalline 10, mp 188°–192°.

I. 17-Cyano-7α,8β-dimethyl-3-methoxymorphinan-6-one(11).

To a solution of 8 (13.30 g, 42 mmol) in chloroform (125 ml) was added potassium carbonate (8.80 g, 67 mmol) followed by the dropwise addition of a solution of cyanogen bormide (5.40 g, 51 mmol) in chloroform (75 ml). The mixture was refluxed for 90 minutes, cooled and filtered from insoluble material. The filtrate was evaporated to dryness and the residue azeotroped several times with ethanol to give crystals. The crystals were boiled with ethanol and collected after cooling to give 10.40 g (75%) of 11 as white needles, mp 159°–161.5°.

J. 17-Cyano-8β-ethyl-3-methoxy-7α-methylmorphinan-6-one (12).

To a mixture of 9 (11.30 g, 34.5 mmol) and potassium carbonate (7.15 g, 51.8 mmol) in chloroform (75 ml) was added dropwise cyanogen bromide (4.45 g, 42.0 mmol) in chloroform. The reaction mixture was refluxed for 2 hours and processed as above to give 10.6 g (86%) of 12 as a foam after azeotroping with EtOH. The foam was used without further characterization in the hydrolysis reaction.

K. 3-Methoxy-7α-methylmorphinan-6-one Hydrochloride (13).

A suspension of 10 (7.2 g, 23 mmol) in 2 N HCl was refluxed for 5 hours. The clear solution was evaporated to give 7.4 g of 13 as a foam, homogeneous by thin layer chromatography, which was used without further purification in the alkylation reactions as described below.

L. 7α,8β-Dimethyl-3-methoxymorphinan-6-one Hydrochloride (14)

Compound 11 (11.2 g, 34.5 mmol) in 2 N HCl (200 ml) was refluxed for 6 hours. The solution was evaporated to a crystalline residue which was triturated with ethanol and collected to give 6.8 g (61%) of 14, mp 235°–240°.

M. 8β-Ethyl-3-methoxy-7α-methylmorphinan-6-one Hydrochloride (15).

Compound 12 (10.6 g, 32.4 mmol) and 2 N HCl (200 ml) was refluxed for 5 hours and the resulting solution evaporated to dryness. Upon coevaporation with ethanol, there was obtained 6.9 g (63%) of crystalline 15, mp>265°.

N. 17-Cyclopropylmethyl-3-methoxy-7α-methylmorphinan-6-one Hydrochloride (16).

A mixture of 13 (4.80 g, 15 mmol), sodium bicarbonate (2.76 g, 32.8 mmol) and cyclopropylmethyl bromide (3.02 g, 22.5 mmol) in DMF (50 ml) was heated at 100° under an argon atmosphere for 16 hours. The suspension was filtered, the filtrate evaporated and the residue partitioned between dilute NH$_4$OH and benzene. The aqueous phase was extracted twice more with benzene and the combined organic phases dried, filtered and evaporated to a glassy residue. This residue was purified by chromatography to give 3.35 g (66%) of the pure free base of 16 as a glass. NMR (CDCl$_3$):

δ 7.10–6.53, m(3), H1, H2, H4,; 3.80, s(3)—OCH₃; 0.85, d(3), 7—CH₃, J=7 Hz.

The HCl salt was prepared by dissolving the free base in ethanol and adding excess concentrated HCl. Evaporation followed by azeotroping with benzene gave a foam which was crystallized and recrystallized from methanol-ethyl acetate to give white, crystalline 16, mp >265°.

Anal. Calcd for $C_{22}H_{29}NO_2 \cdot HCl$: C, 70.29; H, 8.04; N, 3.73. Found: C, 70.72; H, 8.19; N, 3.73.

O.
17-Cyclopropylmethyl-7α,8β-dimethyl-3-methoxymorphinan-6-one Hydrochloride (17)(TR-5188).

A mixture of 14 (5.0 g, 14.9 mmol), sodium bicarbonate (2.76 g, 32.8 mmol), cyclopropylmethyl bromide (3.02 g, 22.5 mmol) in DMF (50 ml) was heated at 100° under argon for 24 hours. Processing as above for 16 gave a syrup which was purified by column chromatography to give 1.71 g (32%) of the free base of 17. The free base was converted to the HCl salt which was isolated as a foam for analysis.

Anal. Calcd for $C_{23}H_{31}NO_2 \cdot HCl$; C, 70.84; H, 8.27; N, 3.59. Found: C, 71.08; H, 8.24; N, 3.47.

P.
17-Cyclobutylmethyl-7α,8β-dimethyl-3-methoxymorphinan-6-one Hydrochloride (18).

Compound 14 (5.0 g), sodium bicarbonate (2.76 g), cyclobutylmethyl bromide (3.33 g) in DMF was reacted as above and processed to give a syrup which was chromatographed to give 4.24 g (78%) of the free base of 18 as a glass. The HCl salt was prepared and crystallized from ethyl acetate to give pure 18, mp 214°–218°.

Anal. Calcd. for $C_{24}H_{33}NO_2 \cdot HCl$; C, 71.35; H, 8.48; N, 3.47. Found: C, 71.54; H, 8.30; N, 3.46.

Q.
17-Cyclobutylmethyl-8β-ethyl-3-methoxy-7α-methylmorphinan-6-one Hydrochloride (19).

A mixture of 15 (3.50 g), sodium bicarbonate (1.26 g), cyclobutylmethyl bromide (1.79 g) in DMF (50 ml) was heated at 100° for 48 hours. Processing as above followed by chromatography gave 2.22 g (59%) of the free base of 19 as a glass. This was converted to 19 which was obtained as a foam.

Anal. Calcd for $C_{25}H_{35}NO_2 \cdot HCl$; C, 71.83; H, 8.65; N, 3.35. Found: C, 71.62; H, 8.62; N, 3.52.

R.
17-Cyclopropylmethyl-3-hydroxy-7α-methylmorphinan-6-one Hydrochloride (20) (TR-5177).

A mixture of 16 (1.16 g, 3.1 mmol) and 48% HBr (10 ml) was refluxed for 10 minutes in a pre-heated oil bath (140°). The solution was cooled, diluted with water, made basic with concentrated NH₄OH and extracted three times with chloroform. The combined chloroform extracts were dried, filtered and evaporated to a residue which was chromatographed to yield 0.43 g (43%) of the free base of 20 as a glass. The glass was converted to the HCl salt and crystallized from MeOH to give fine needles of 20, mp 217°–220° dec.

Anal. Calcd for $C_{21}H_{27}NO_2 \cdot HCl$: C, 69.69; H, 7.80; N, 3.87. Found: C, 69.64; H, 7.80; N, 3.88.

S.
17-Cyclopropylmethyl-7α,8β-dimethyl-3-hydroxymorphinan-6-one (21) (TR-5196).

Compound 17 (1.0 g, 2.6 mmol) was refluxed with 48% HBr (10 ml) for 10 minutes. After cooling the mixture was diluted with water and adjusted to pH 12 with concentrated NH₄OH, extracted twice with chloroform and then twice with ethyl acetate. The combined organic extracts were dried, filtered and evaporated and the residue partially purified by column chromatography. The resulting foam, which showed a faster migrating minor component together with the desired product, was further purified by preparative layer chromatography on 2 mm layers of Silica Gel G using 15:1 chloroform-methanol containing 0.75L % concentrated NH₄OH as the eluant. Development was repeated 5 times. The major spot was extracted from the gel by use of boiling methanol. The residue obtained on evaporation of the methanol was again column chromatographed to yield 0.26 g of 21 as a white foam.

Anal. Calcd. for $C_{22}H_{29}NO_2$: C, 77.84; H, 8.61; N, 4.13. Found: C, 76.82; H, 8.61; N, 4.33.

T.
17-Cyclobutylmethyl-7α,8β-dimethyl-3-hydroxymorphinan-6-one (22) (TR-5195).

Compound 16 (2.04 g, 5.6 mmol) and 48% HBr (20 ml) was refluxed for 20 minutes. Workup as above gave a foam which was chromatographed to give 1.50 g (76%) of pure 22 as a foam.

Anal. Calcd. for $C_{23}H_{31}NO_2$: C, 78.15; H, 8.84; N, 3.96. Found: 78.11; H, 9.09; N, 3.87.

U.
17-Cyclobutylmethyl-8β-ethyl-3-hydroxy-7α-methylmorphinan-6-one (23) (TR-5333)

Compound 17 (1.80 g, 4.3 mmol) and 48% HBr (20 ml) was refluxed for 15 minutes and processed in the usual fashion to give a foam. The foam was crystallized from ethanol to give 1.37 g (79%) of crystalline 23, mp 120°–122°, as the ethanol solvate. Drying gave 23.0.75 EtOH (as indicated by nmr) which was submitted for analysis.

Anal. Calcd. for $C_{24}H_{33}NO_2 \cdot 0.75$ EtOH: C, 76.17 H, 9.40; N, 3.48. Found: C, 76.18; H, 9.45; N, 3.22.

EXAMPLE 8
Preparation of 17-Cyclopropylmethyl and Cyclobutylmethyl 7β-Methyl and 7β-Methyl-8α-Lower Alkyl Isomorphinane-6-One-Compounds A. 7β,17-Dimethyl-3-methoxy-isomorphinan-6-one (24).

A solution of 6 (10.8 g, 36.3 mmol) in 95% ethanol (250 ml) containing concentrated HCl (0.5 ml) was hydrogenated over 10% palladium on charcoal (1.0 g) at 50 psi. Removal of the catalyst followed by evaporation of the filtrate gave a foam which was partitioned between dilute NH₄OH and chloroform. Several further extractions with chloroform followed by evaporation of the organic phases gave a crystalline residue which was recrystallized from ethyl acetate to give 8.7 g (81%) of 24 as white needles, mp 175°–176°. NMR (CDCl₃); δ 7.23–6.63, m(3), H1, H2, H4; 3.82, s(3), —OCH₃; 2.37, s(3), —NCH₃; 1.08, d(3), 7—CH₃, J=6 Hz.

Anal. Calcd. for $C_{19}H_{25}NO_2$: C, 76.22; H, 8.42; N, 4.68. Found: C, 76.33; H, 8.41; N, 4.66.

B. 3-Methoxy-7β,8α,17-trimethyl-isomorphinan-6-one Hydrochloride (25).

To a solution of lithium dimethyl cuprate, prepared from copper iodide (1.20 g, 6.3 mmol) and methyl lithium (12.6 mmol), in ether (75 ml) was added compound 6 (1.50 g, 5 mmol) in benzene (75 ml). After 1 hour at 0°, workup in the usual manner followed by column chromatography gave 1.35 g (86%) of 25 free base as a foam. This was converted to the HCl salt and crystallized from ethanol-ethyl acetate to give pure 25, mp >265°. NMR ($CDCl_3$): δ 7.20–6.57, m(3), H1, H2, H4; 3.80, s(3), —$OCH_3$; 2.70, s(3), —$NCH_3$; 1.13, d(6), 7 and 8—$CH_3$, J=6 Hz.

Anal. Calcd. for $C_{20}H_{27}NO_2·HCl$: C, 68.65; H, 8.06; N, 4.00. Found: C, 68.35; H, 7.93; N, 3.83.

C.
7β,17-Dimethyl-8α-ethyl-3-methoxy-isomorphinan-6-one Hydrochloride (26).

Vinyl lithium was prepared from vinyl bromide (3.0 ml, 42 mmol) and t-butyllithium (85 mmol) in ether (60 ml) by stirring for 1 hour at −78° under argon. This was transferred to a −78° suspension of copper iodide (4.00 g, 21 mmol) in ether (100 ml). The mixture was allowed to warm to −40° and while maintaining this temperature, a solution of 6 (5.0 g, 16.8 mmol) in methylene chloride (100 ml) was added dropwise. The reaction mixture was left at −40° for 15 minutes and then allowed to warm to room temperature. Workup in the usual fashion gave a foam which consisted of 2 major spots as shown by thin layer chromatography for the 1,2 and 1,4 addition products. The foam was dissolved in 95% ethanol (250 ml), concentrated HCl (0.5 ml) and 10% palladium on charcoal added and the mixture hydrogenated at 50 psi for 8 hr. Processing in the usual manner followed by chromatography gave 1.57 g (28%) of the free base of 26 as a foam. The foam was converted to the HCl salt which crystallized from methanol-ethyl acetate to give pure 26, mp 249°–250° dec. NMR ($CDCl_3$): δ 7.23–6.53 m(3), H1, H2, H4; 3.80, s(3), —$OCH_3$; 2.37, s(3), —$NCH_3$; 1.40–0.67, m(8) 7—$CH_3$, 8—$CH_2CH_3$.

Anal. Calcd. for $C_{21}H_{29}NO_2·HCl$: C, 69.31; H, 8.31; N, 3.85. Found: C, 69.02; H, 8.45; N, 3.93.

D.
17-Cyano-7β-methyl-3-methoxy-isomorphinan-6-one (27).

To a solution of 24 (8.7 g, 29 mmol) in chloroform (100 ml) containing potassium carbonate (6.1 g, 44 mmol) was added dropwise a solution of cyanogen bromide (3.1 g, 37 mmol) in chloroform (50 ml). After completion of the addition, the mixture was refluxed for 3 hours, cooled and filtered from the insoluble material. The filtrate was evaporated to dryness and repeatedly azeotroped with ethanol until crystals formed. The solution was cooled and 5.9 g (66%) of white crystalline 27 collected. This material was used as is in the hydrolysis step to prepare 30.

E.
17-Cyano-7β,8α-dimethyl-3-methoxy-isomorphinan-6-one (28).

A solution of 25 (free base, 10.4 g, 33.2 mmol) in chloroform (75 ml) containing potassium carbonate (6.9 g, 50 mmol) was treated dropwise with cyanogen bromide (4.3 g, 40 mmol) in chloroform (50 ml). The mixture was refluxed for 4 hr, cooled and filtered from the insoluble material. The filtrate was evaporated to dryness and the residue chromatographed to give 4.83 g (45%) of 28 as a foam.

F.
17-Cyano-8α-ethyl-3-methoxy-7β-methyl-isomorphinan-6-one (29).

To a solutiona of 26 (free base, 19.7 g, 60.2 mmol) in chloroform (250 ml) containing potassium carbonate (12.5 g, 90.2 mmol) was added dropwise a solution of cyanogen bromide (7.7 g, 72.2 mmol) in chloroform (100 ml). The mixture was then refluxed for 3 hours, cooled and the insoluble material removed by filtration. The filtrate was evaporated to dryness and the residue purified by column chromatography to give 10.8 g (52%) of 29 as a foam.

G. 3-Methoxy-7β-methyl-isomorphinan-6-one (30).

A mixture of 27 (5.9 g) and 2 N HCl (200 ml) was refluxed overnight. The mixture was concentrated to a small volume and the residue partitioned between dilute $NH_4OH$ and chloroform. The chloroform extracts were evaporated to give 5.5 g of 30 as a glass, homogeneous by thin layer chromatography. This material was used as is in the preparation of 33.

H. 7β,8α-Dimethyl-3-methoxy-isomorphinan-6-one (31).

A mixture of 28 (4.7 g) and 2 N HCl (200 ml) was refluxed overnight and processed as above. The resulting foam was chromatographed to give 2.83 g of 31 which crystallized on standing. This material was used in further reactions without additional characterization.

I. 8α-Ethyl-3-methoxy-7β-methyl-isomorphinan-6-one (32).

The N-cyano compound 29 (10.7 g) and 2 N HCl (400 ml) was refluxed for 24 hr. The clear solution was cooled, made basic with concentrated $NH_4OH$ and extracted with chloroform. The chloroform extracts were evaporated to give 10.0 g of 35 as a foam, homogeneous by thin layer chromatography which was used without further purification for the preparation of 36.

J.
17-Cyclopropylmethyl-3-methoxy-7β-methyl-isomorphinan-6-one Hydrochloride (33) (TR-5205).

To a solution of 30 (2.70 g, 9.5 mmol) in DMF (50 ml) was added sodium bicarbonate (0.80 g, 9.5 mmol) and cyclopropylmethyl bromide (1.55 g, 11.4 mmol) in DMF (5 ml). The mixture was heated at 100° overnight in an argon atmosphere. The cooled solution was filtered from insoluble material and the bulk of the DMF removed under high vacuum. The residue was dissolved in dilute $NH_4OH$ and extracted with three portions of toluene. The toluene was dried, filtered and evaporated to a foam. The foam was dissolved in ethanol and converted to the HCl salt by the addition of concentrated HCl. The solvent was removed and the residue azeotroped first with ethanol then 1:1 ethanol-toluene followed by toluene. This residual material was crystallized from methanol-ethyl acetate to give 1.86 g (52%) of 33, mp 165°–177°. Recrystallization from the same solvent pair gave pure 33, mp 174.5°–177°.

Anal. Calcd. for $C_{22}H_{29}NO_2 \cdot HCl$: C, 70.29; H, 8.04; N, 3.73. Found: C, 70.30; H, 8.07; N, 3.59.

K. 17-Cyclopropylmethyl-7β,8α-dimethyl-3-methoxy-isomorphinan-6-one Hydrochloride (34) (TR-5331).

A mixture of 31 (1.84 g, 6.1 mmol) in DMF (35 ml) containing sodium bicarbonate (0.78 g, 9.2 mmol) and cyclopropylmethyl bromide (1.00 g, 7.4 mmol) was heated at 100° under an argon atmosphere for 17 hours. Processing as above for 33 gave a syrup which was converted to the HCl salt and crystallized from methanol-ethyl acetate to give 1.68 g (71%) of pure 34, mp >265°.

Anal. Calcd. for $C_{23}H_{31}NO_2 \cdot HCl$: C, 70.84; H, 8.27; N, 3.59. Found: C, 71.07; H, 8.34; N, 3.81.

L. 17-Cyclobutylmethyl-7β,8α-dimethyl-3-methoxy-isomorphinan-6-one Hydrochloride (35) (TR-5332).

Prepared from compound 31 (1.84 g, 6.1 mmol) and cyclobutylmethyl bromide (1.10 g, 7.4 mmol) in DMF (35 ml) containing sodium bicarbonate (0.78 g, 9.2 mmol) at 100° overnight. Workup in the usual fashion gave 1.96 g (86%) of the free base of 38 as a glass which was converted to the HCl salt and crystallized from methanol-ethyl acetate to give pure 35, mp >265°.

Anal. Calcd. for $C_{24}H_{33}NO_2 \cdot HCl$: C, 71.35; H, 8.48; N, 3.47. Found: C, 71.13; H, 8.48; N, 3.36.

M. 17-Cyclobutylmethyl-8α-ethyl-3-methoxy-7β-methyl-isomorphinan-6-one Hydrochloride (36).

Compound 35 (3.70 g, 11.8 mmol), sodium bicarbonate (2.48 g, 29.5 mmol) and cyclobutylmethyl bromide (2.11 g, 14.2 mmol) in DMF (65 ml) were reacted in the usual fashion for 6.5 hours. Workup as previously described gave 3.84 g (85%) of the free base of 36 as a glass. This was converted to the HCl salt which was twice recrystallized from methanol-ethyl acetate to give pure 36, mp >265°.

Anal. Calcd. for $C_{25}H_{35}NO_2 \cdot HCl$: C, 71.83; H, 8.68; N, 3.35. Found: C, 71.43; H, 8.89; N, 3.22.

N. 17-Cyclopropylmethyl-3-hydroxy-7β-methyl-isomorphinan-6-one Hydrobromide (37) (TR-5225).

A mixture of 33 (4.2 g) and 48% HBr (25 ml) was refluxed in an oil bath preheated to 140° for 20 minutes. The resulting suspension was cooled and filtered to give 3.31 g of white crystals. The crystals were converted to the free base and further purified by chromatography to give the free base of 37 as a foam. This foam was converted to the HBr salt in a manner analogous to that used for the HCl salts. Crystallization from aqueous ethanol gave pure 37, mp >265°.

Anal. Calcd. for $C_{21}H_{27}NO_2 \cdot HBr$: C, 62.07; H, 6.95; N, 3.45. Found: C, 62.15; H, 6.99; N, 3.36.

O. 17-Cyclopropylmethyl-7β,8α-dimethyl-3-hydroxy-isomorphinan-6-one Hydrobromide (38) (TR-5343).

A mixture of 34 (free base, 2.44 g) and 48% HBr (25 ml) was refluxed for 15 minutes. The solution was cooled and the crystalline 38 (2.21 g, 76%) collected. The crystals, mp >270°, were purified by boiling with aqueous methanol.

Anal. Calcd. for $C_{22}H_{29}NO_2 \cdot HBr$: C, 62.86; H, 7.19; N, 3.33. Found: C, 62.53; H, 7.15; N, 3.06.

P. 17-Cyclobutylmethyl-8α-ethyl-3-hydroxy-7β-methyl-isomorphinan-6-one Hydrochloride (39) (TR-5370).

A mixture of 36 (2.1 g) and 48% HBr (20 ml) was refluxed for 20 minutes then processed as above and chromatographed to give 873 mg (43%) of the free base of 39. This was converted to the HCl salt which crystallized from methanol-ethyl acetate to give pure 39, mp >270°.

Anal. Calcd. for $C_{24}H_{33}NO_2 \cdot HCl$: C, 71.35; H, 8.48; N, 3.47. Found: C, 71.05; H, 8.52; N, 3.39.

EXAMPLE 9

PHARMACOLOGICAL EVALUATION

The compounds whose preparation is disclosed in the foregoing examples were screened to determine the following biological activities:

(A) Analgesic effects upon mice (acetic acid writhing test).

(B) Narcotic antagonist activity in rats (modified rat tail flick test).

TEST A. ACETIC ACID MOUSE WRITHING TEST

The analgesic effects of test compounds were determined in mice by use of the acetic acid writhing test described by B. J. R. Whittle, Brit. J. Pharmacol., 22:246 (1964). In this test at least three groups of five male CD-1 mice (18–22 g) each were given subcutaneous doses of the test drug dissolved in either distilled water or distilled water acidified with HCl depending on the solubility of the compound. In all cases, 0.4 milliliter of a 0.5% V/V acetic acid in distilled water solution was administered intraperitoneally 15 minutes post drug. The number of writhes in a 20 min. interval beginning 5 minutes after the acetic acid injection were determined and compared with the number of writhes in control groups which had received only acetic acid.

Percent inhibition of writhing was calculated as:

$$\% \text{ inhibition} = \frac{\text{No. Control writhes} - \text{No. treated writhes}}{\text{No. control writhes}} \times 100$$

The $ED_{50}$ dose, i.e., the dose required to reduce the number of writhes by 50%, was determined graphically from a plot of % inhibition as a probit versus log dose. Confidence limits of 95% were calculated on the basis of those results falling in the range 16–84% inhibition. See Litchfield, J. T. and Wilcoxon, F., J. Pharmacol. Exp. Ther., 96, 99–113, (1949).

TEST B. EVALUATION OF NARCOTIC ANTAGONIST ACTIVITY

The narcotic antagonist effects of test compounds were determined by a modification of the rat tail flick procedure of Harris and Pierson (J. Pharmacol. Exp. Ther. 143:141 [1964]).

Male albino Wistar rats (100–120 g) were used for this study. A rat's tail is so placed so as to cover a photocell. Heat is applied by a lamp in a reflector with a timer being connected to the lamp and photocell so that the timer goes on when the light is turned on and is turned off when the photocell is uncovered. A rheostat, incorporated into a heating lamp is used to adjust the intensity of the light falling on the tail of the rat such that the rat's control reaction time is from two to four seconds.

Animals with a control reaction time outside this range are rejected. The rheostat adjustment is made only if a significant proportion (more than 2 out of every 10 rats) of the reaction times are outside the range of two to four seconds. Groups of five rats were used each time, and two control times were determined at 60 and 30 minutes prior to subcutaneous injection of the drug. A ten second cutoff time is employed; if the rat does not flick its tail in 10 seconds it is removed from the heat source.

Thirty minutes after the last control run the test drug was given intraperitoneally. This was followed ten minutes later by an $ED_{80}$ dose of morphine subcutaneously. The animals were retested at 20 minutes after the morphine injection. Control animals were given vehicle and morphine only. The data were calculated as follows:

$$\% \text{ Effect } (E) = \frac{[MRT^* \text{ (Treated)} - MRT \text{ (Control)}] \times 100}{10 \text{-} MRT \text{ (Control)}}$$

$$\% \text{ Antagonism } = \frac{[E \text{ (morphine controls)} - E \text{ (drug treated)}] \times 100}{E \text{ (morphine control)}}$$

*MRT is defined as mean reaction time.

The data were plotted on log-probit paper and $AD_{50}$ values, i.e., the dose required to inhibit the morphine effect by 50% within 95% confidence limits, were determined by the method of Litchfield and Wilcoxon.

The results of these experiments are set out in Table I where $R_1$, $R_2$, $R_3$ and $R_4$ refer to the preceding Formula I for the compounds of the present invention. In the column under $R_2$, CBM stands for cyclobutylmethyl, CPM for cyclopropylmethyl. For purposes of this table, IA is intended to mean "inactive" at the dose indicated.

TABLE I

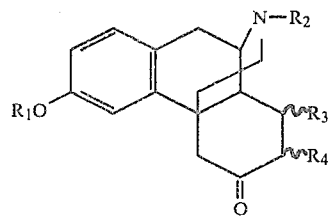

| Compound | Ex. | B/C | $R_1$ | $R_2$ | $R_3$ | $R_4$ | $ED_{50}$ | $AD_{50}$ |
|---|---|---|---|---|---|---|---|---|
| TR-5148 | 6I | Cis* | $CH_3$ | CBM | H | H | 0.22 | IA @ 10 |
| TR-5153 | 6II | Cis* | H | CBM | H | H | 0.017 | IA @ 10 |
| TR-5152 | 6III | Cis* | $CH_3$ | CPM | H | H | 0.24 | 5.4 |
| TR-5160 | 6IV | Cis* | H | CPM | H | H | 1.02 | 2.3 |
| TR-5222 | 6V | trans* | H | CPM | H | H | 3.11** | 0.78 |
| TR-5223 | 6VI | trans* | H | CBM | H | H | 0.94 | 5.0 |
| TR-5130 | 3 | Cis | H | CBM | $\beta$-$CH_3$ | H | 0.11 | 1.05 |
| TR-5132 | 2 | Cis | $CH_3$ | CBM | $\beta$-$CH_3$ | H | 0.54 | 6.4 |
| TR-5119 | 1D | Cis | $CH_3$ | CPM | $\beta$-$CH_3$ | H | 0.24 | 1.45 |
| TR-5200 | 4 | Cis | H | CBM | $\beta$-ethyl | H | 0.21 | 0.32 |
| TR-5204 | 5 | Cis | H | CBM | $\beta$-n-prop | H | 0.43 | 3.10 |
| TR-5343 | 8O | trans | H | CPM | $\alpha$-$CH_3$ | $\beta$-$CH_3$ | 1.89 | 0.43 |
| TR-5225 | 8N | trans | H | CPM | H | $\beta$-$CH_3$ | 0.72** | 0.48 |
| TR-5333 | 7U | Cis | H | CBM | $\beta$-ethyl | $\alpha$-$CH_3$ | 3.3 | 1.95 |
| TR-5195 | 7T | Cis | H | CBM | $\beta$-$CH_3$ | $\alpha$-$CH_3$ | 0.78 | 2.0 |
| TR-5177 *** | 7R | Cis | H | CPM | H | $\alpha$-$CH_3$ | 0.87 | 5.2 |
| TR-5188 | 7O | Cis | $CH_3$ | CPM | $\beta$-$CH_3$ | $\alpha$-$CH_3$ | 1.03 | 4.7 |
| TR-5205 | 8J | trans* | $CH_3$ | CPM | H | $\beta$-$CH_3$ | >15 | 1.2 |
| TR-5331 | 8K | trans* | $CH_3$ | CPM | $\alpha$-$CH_3$ | $\beta$-$CH_3$ | >10 | >10 |
| TR-5332 | 8L | trans* | $CH_3$ | CBM | $\alpha$-$CH_3$ | $\beta$-$CH_3$ | >10 | >10 |
| TR-5370 | 8P | trans* | H | CBM | $\alpha$-ethyl | $\beta$-$CH_3$ | IA @ 10 | >10 |
| TR-5196 | 7S | Cis* | H | CPM | $\beta$-$CH_3$ | $\alpha$-$CH_3$ | 7.8 | 0.12 |

*reference compounds
**short acting
***novel action in charcoal meal test upon attempted naloxone reversal (TR-5177)

In comparing the presently claimed compounds with those compounds which are most closely related structurally (referred to for purposes of this application as reference compounds) the following conclusions can be drawn:

TR-5130 which differs structurally from TR-5153 by the substitution of a $\beta$-methyl group in the 8 position possesses mixed agonist/antagonist activity whereas TR-5153 is a pure agonist. The B/C trans isomer of TR-5153; i.e., TR-5223, does show mixed agonist/antagonist activity but this activity is substantially less than that of TR-5130.

TR-5132 which differs from TR-5148 by the substitution of hydrogen with a $\beta$-methyl group at the 8-position exhibits good activity as both an analgesic and a narcotic antagonist whereas TR-5148 is a potent analgesic but does not exhibit activity as a narcotic antagonist.

TR-5119 which differs from TR-5152 by the substitution of hydrogen with a $\beta$-methyl group at the 8-position shows good activity as both an analgesic and a narcotic antagonist whereas TR-5152 has substantially less antagonist activity.

TR-5200 which differs from TR-5153 by the substitution of H with $\beta$-ethyl at the 8 position exhibits potent activity as both an analgesic and a narcotic antagonist whereas TR-5153 is a pure agonist. TR-5223 which is similar to TR-5153 but is B/C trans rather than B/C cis exhibits mixed analgesic/narcotic antagonist activity but is significantly less potent in both respects than is TR-5200.

TR-5204 which is the 8$\beta$-n-propyl derivative of TR-5153 is a mixed analgesic/narcotic antagonist whereas TR-5153 is a pure analgesic. Comparing TR-5204 with the B/C trans form of TR-5153, i.e., TR-5223 indicates that TR-5204 is substantially more potent in both respects.

TR-5343 differs from TR-5222 by the substitution of the 7 and 8 hydrogen atoms with $\beta$-CH$_3$ and $\alpha$-methyl, respectively. While both compounds exhibit mixed analgesic and narcotic antagonist activity, TR-5343 is more potent in both respects by a factor of approximately two. It is also significant that TR-5331 which differs from TR-5343 by the substitution of a methyl group for hydrogen at the 3-position is essentially inactive either as an analgesic or a narcotic antagonist. In addition TR-5343 is approximately 4 times as potent as an analgesic although somewhat less potent a narcotic antagonist at its geometric isomer, TR-5196.

TR-5225 which differs from TR-5222 by the replacement of a 7-hydrogen atom with a $\beta$-methyl group is more potent as an analgesic by a factor of greater than four and more potent as a narcotic antagonist by a factor of approximately 2. Comparing TR-5225 with TR-5205 from which it differs by a hydrogen atom rather than a methyl group at the 3-position, it can be seen that TR-5225 is much more potent as an analgesic and approximately twice as potent a narcotic antagonist.

TR-5333 exhibits both analgesic and narcotic antagonist activity whereas TR-5153 from which it differs by the replacement of hydrogen with $\alpha$-methyl at the 7-position and $\beta$-CH$_2$CH$_3$ at the 8-position is a pure analgesic. Comparing TR-5333 with its geometric isomer TR-5370, reveals that the geometric isomer of TR-5333 is essentially inactive as either an analgesic or a narcotic antagonist.

TR-5195, which differs from TR-5153 by the substitution of hydrogen with $\alpha$-methyl and $\beta$-methyl at the 7- and 8-position, respectively, exhibits analgesic and narcotic antagonist activity whereas TR-5153 is a pure analgesic.

TR-5188 which differs from TR-5152 by the substitution of hydrogen with $\alpha$-methyl and $\beta$-methyl at the 7- and 8-position, respectively, is a mixed analgesic/narcotic antagonist whereas TR-5152 is a weaker antagonist. The geometric isomer of TR-5188, TR-5331, is essentially inactive as either an analgesic or a narcotic antagonist.

The novel action in the charcoal meal test upon attempted reversal with naloxone suggests that TR-5177 may have a longer duration of action than would be expected for a compound of this type.

What is claimed is:

1. 7-methyl, 8$\beta$-lower alkyl and 7-methyl-8-lower alkyl substituted B/C cis or trans morphinan-6-one compounds characterized by the structural formula:

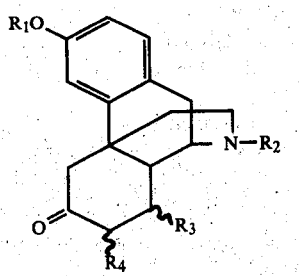

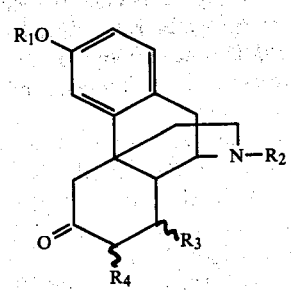

wherein R$_1$ is H or methyl, R$_2$ is cyclopropylmethyl or cyclobutylmethyl, R$_3$ is H, methyl, ethyl or n-propyl and R$_4$ is H or methyl, provided that:

A. when the molecule is in the B/C cis configuration and R$_2$ is cyclobutylmethyl,
 i. R$_3$ is $\beta$-methyl, $\beta$-ethyl or $\beta$-n-propyl when R$_1$ and R$_4$ are H,
 ii. R$_1$ is methyl only when R$_4$ is H and R$_3$ is $\beta$-methyl, and
 iii. when R$_4$ is $\alpha$-methyl, R$_1$ is H and R$_3$ is $\beta$-methyl or $\beta$-ethyl,
B. when the molecule is in the B/C cis configuration and R$_2$ is cyclopropylmethyl,
 i. R$_3$ is $\beta$-methyl and R$_4$ is H or $\alpha$-methyl when R$_1$ is methyl, and
 ii. R$_3$ is H and R$_4$ is $\alpha$-methyl when R$_1$ is H; and
C. when the molecule is in the B/C trans configuration, R$_1$ is H and R$_2$ is cyclopropylmethyl,
 i. R$_3$ is either $\alpha$-methyl or H, and
 ii. R$_4$ is $\beta$-methyl.

2. The compounds of claim 1 in the form of their organic or inorganic pharmaceutically acceptable acid addition salts.

3. A compound as defined by claim 1 wherein R$_1$ is H, R$_2$ is cyclobutylmethyl, R$_3$ is $\beta$-methyl and R$_4$ is H and is in the B/C cis configuration.

4. The hydrochloric acid and tartaric acid salts of the compound defined by claim 3.

5. A compound as defined by claim 1 wherein R$_1$ is CH$_3$, R$_2$ is cyclobutylmethyl, R$_3$ is $\beta$-methyl and R$_4$ is H and which is in the B/C cis configuration.

6. The hydrochloric acid salt of the compound defined by claim 5.

7. A compound as defined by claim 1 wherein R$_1$ is methyl, R$_2$ is cyclopropylmethyl, R$_3$ is $\beta$-methyl and R$_4$ is H and is in the B/C cis configuration.

8. The hydrochloric acid salt of the compound defined by claim 7.

9. A compound as defined by claim 1 wherein R$_1$ is H, R$_2$ is cyclobutylmethyl, R$_3$ is $\beta$-ethyl and R$_4$ is H and is in the B/C cis configuration.

10. The hydrochloric acid addition salt of the compound defined by claim 9.

11. A compound as defined by claim 1 wherein R$_1$ is H, R$_2$ is cyclobutylmethyl, R$_3$ is $\beta$-n-propyl and R$_4$ is H and which is in the B/C cis configuration.

12. The hydrochloric acid addition salt of the compound defined by claim 11.

13. A compound as defined by claim 1 wherein R$_1$ is H, R$_2$ is cyclopropylmethyl, R$_3$ is $\alpha$-methyl and R$_4$ is $\beta$-methyl and which is in the B/C trans configuration.

14. The hydrobromic acid addition salt of the compound defined by claim 13.

15. A compound as defined by claim 1 wherein $R_1$ is H, $R_2$ is cyclopropylmethyl, $R_3$ is H and $R_4$ is β-methyl and which is in the B/C trans configuration.

16. The hydrobromic acid addition salt of the compound defined by claim 15.

17. A compound as defined by claim 1 wherein $R_1$ is H, $R_2$ is cyclobutylmethyl, $R_3$ is β-ethyl and $R_4$ is α-methyl and which is in the B/C cis configuration.

18. A compound as defined by claim 1 wherein $R_1$ is H, $R_2$ is cyclobutylmethyl, $R_3$ is β-methyl and $R_4$ is α-methyl and which is in the B/C cis configuration.

19. A compound as defined by claim 1 wherein $R_1$ is H, $R_2$ is cyclopropylmethyl, $R_3$ is H and $R_4$ is α-methyl and which is in the B/C cis configuration.

20. The hydrochloric acid addition salt of the compound defined by claim 19.

21. A compound as defined by claim 1 wherein $R_1$ is methyl, $R_2$ is cyclopropylmethyl, $R_3$ is β-methyl and $R_4$ is α-methyl and which is in the B/C cis configuration.

22. The hydrochloric acid addition salt of the compound defined by claim 21.

23. A therapeutic method of treating pain in an individual requiring such treatment which comprises administering to such individual an effective amount of a compound characterized by the formula:

wherein $R_1$ is H or methyl, $R_2$ is cyclopropylmethyl or cyclobutylmethyl, $R_3$ is H, methyl, ethyl or n-propyl and $R_4$ is H or methyl, provided that:
A. when the molecule is in the B/C cis configuration and $R_2$ is cyclobutylmethyl,
  i. $R_3$ is β-methyl, β-ethyl or β-n-propyl when $R_1$ and $R_4$ are H,
  ii. $R_1$ is methyl only when $R_4$ is H and $R_3$ is β-methyl, and
  iii. when $R_4$ is α-methyl, $R_1$ is H and $R_3$ is β-methyl or β-ethyl;
B. when the molecule is in the B/C cis configuration and $R_2$ is cyclopropylmethyl,
  i. $R_3$ is β-methyl and $R_4$ is H or α-methyl when $R_1$ is methyl, and
  ii. $R_3$ is H and $R_4$ is α-methyl when $R_1$ is H, and
C. when the molecule is in the B/C trans configuration, $R_1$ is H and $R_2$ is cyclopropylmethyl,
  i. $R_3$ is either α-methyl or H, and
  ii. $R_4$ is β-methyl.

24. The method of claim 23 wherein the compound is administered in the form of its organic or inorganic pharmaceutically acceptable acid addition salt.

25. The method as defined by claim 23 wherein the compound administered is characterized in that $R_1$ is H, $R_2$ is cyclobutylmethyl, $R_3$ is β-methyl and $R_4$ is H and is in the B/C cis configuration.

26. The method of claim 25 wherein the compound administered is in the form of its hydrochloric acid addition salt.

27. The method as defined by claim 23 wherein the compound administered is characterized in that $R_1$ is methyl, $R_2$ is cyclobutylmethyl, $R_3$ is β-methyl and $R_4$ is H and is in the B/C cis configuration.

28. The method of claim 27 wherein the compound is administered in the form of its hydrochloric acid addition salt.

29. The method as defined by claim 23 wherein the compound administered is characterized in that $R_1$ is H, $R_2$ is cyclobutylmethyl, $R_3$ is β-ethyl and $R_4$ is H and is in the B/C cis configuration.

30. The method of claim 29 wherein the compound is administered in the form of its hydrochloric acid addition salt.

31. The method as defined by claim 23 wherein the compound administered is characterized in that $R_1$ is H, $R_2$ is cyclobutylmethyl, $R_3$ is β-n-propyl and $R_4$ is H and is in the B/C cis configuration.

32. The method of claim 31 wherein the compound is administered in the form of its hydrochloric acid addition salt.

33. The method as defined by claim 23 wherein the compound administered is characterized in that $R_1$ is H, $R_2$ is cyclopropylmethyl, $R_3$ is α-methyl and $R_4$ is β-methyl and is in the B/C trans configuration.

34. The method as defined by claim 33 wherein the compound is administered in the form of its hydrobromic acid addition salt.

35. The method as defined by claim 23 wherein the compound administered is characterized in that $R_1$ is H, $R_2$ is cyclopropylmethyl, $R_3$ is H and $R_4$ is β-methyl and is in the B/C trans configuration.

36. The method as defined by claim 35 wherein the compound is administered in the form of its hydrobromic acid addition salt.

37. The method as defined by claim 23 wherein the compound administered is characterized in that $R_1$ is H, $R_2$ is cyclobutylmethyl, $R_3$ is β-ethyl and $R_4$ is α-methyl and is in the B/C cis configuration.

38. The method as defined by claim 23 wherein the compound administered is characterized in that $R_1$ is H, $R_2$ is cyclobutylmethyl, $R_3$ is β-methyl and $R_4$ is α-methyl and is in the B/C cis configuration.

39. The method as defined by claim 23 wherein the compound administered is characterized in that $R_1$ is H, $R_2$ is cyclopropylmethyl, $R_3$ is H and $R_4$ is α-methyl and is in the B/C cis configuration.

40. The method as defined by claim 39 wherein the compound is administered in the form of its hydrobromic acid addition salt.

41. The method as defined by claim 23 wherein the compound administered is characterized in that $R_1$ is methyl, $R_2$ is cyclopropyl methyl, $R_3$ is β-methyl and $R_4$ is H and is in the B/C cis configuration.

42. The method as defined by claim 41 wherein the compound is administered in the form of its hydrochloric acid addition salt.

43. The method as defined by claim 23 wherein the compound administered is characterized in that $R_1$ is methyl, $R_2$ is cyclopropylmethyl, $R_3$ is β-methyl and $R_4$ is α-methyl and is in the B/C cis configuration.

44. The method as defined by claim 4 wherein the compound is administered in the form of its hydrochloric acid addition salt.

* * * * *